(12) United States Patent
Weng

(10) Patent No.: US 10,617,828 B2
(45) Date of Patent: Apr. 14, 2020

(54) MEDICAL INJECTION DEVICE

(71) Applicant: Jian-Sen Weng, Taoyuan (TW)

(72) Inventor: Jian-Sen Weng, Taoyuan (TW)

( * ) Notice: Subject to any disclaimer, the term of this patent is extended or adjusted under 35 U.S.C. 154(b) by 292 days.

(21) Appl. No.: 15/655,744

(22) Filed: Jul. 20, 2017

(65) Prior Publication Data

US 2018/0021522 A1 Jan. 25, 2018

(30) Foreign Application Priority Data

| Jul. 21, 2016 | (CN) | 2016 2 0773271 U |
| Jul. 21, 2016 | (CN) | 2016 2 0773474 U |
| May 17, 2017 | (CN) | 2017 2 0547256 U |
| May 27, 2017 | (CN) | 2017 2 0606431 U |

(51) Int. Cl.
*A61M 5/315* (2006.01)
*A61M 5/24* (2006.01)
*A61M 5/32* (2006.01)
*A61M 5/31* (2006.01)

(52) U.S. Cl.
CPC .......... *A61M 5/31586* (2013.01); *A61M 5/24* (2013.01); *A61M 5/2422* (2013.01); *A61M 5/31541* (2013.01); *A61M 5/31551* (2013.01); *A61M 5/3204* (2013.01); *A61M 5/3257* (2013.01); *A61M 2005/2492* (2013.01); *A61M 2005/3126* (2013.01); *A61M 2205/0216* (2013.01)

(58) Field of Classification Search
CPC ................ A61M 5/20; A61M 5/31525; A61M 5/31526; A61M 5/31528; A61M 5/31548; A61M 5/31551; A61M 5/31555; A61M 5/31565; A61M 5/61585; A61M 2005/2407; A61M 5/3257; A61M 5/31586; A61M 5/24; A61M 5/2422; A61M 5/31541; A61M 5/3204; A61M 2005/2026; A61M 5/2492; A61M 5/3126
See application file for complete search history.

(56) References Cited

U.S. PATENT DOCUMENTS

| 2009/0247951 A1* | 10/2009 | Kohlbrenner ........... A61M 5/20 604/134 |
| 2014/0039410 A1* | 2/2014 | Harms ............... A61M 5/31583 604/211 |
| 2015/0051551 A1* | 2/2015 | Hirschel ............. A61M 5/3156 604/189 |

* cited by examiner

*Primary Examiner* — Nathan R Price
*Assistant Examiner* — Dung T Ulsh
(74) *Attorney, Agent, or Firm* — CBM Patent Consulting, LLC

(57) ABSTRACT

A medical injection device, comprising: a housing having a first end cover and a second end cover provided at two ends thereof, respectively; a dial threaded rod, which is in threaded connected to the first end cover; and, a piston rod, which is used for expelling a dose, an upper end of the piston rod being connected to the dial threaded rod through a driving mechanism while a lower end thereof is in threaded connected to the second end cover. It further comprises a dosage adjustment mechanism, which is arranged between the dial threaded rod and the housing and used for driving the dial threaded rod to move in an axial direction of the housing.

41 Claims, 23 Drawing Sheets

MEDICAL INJECTION DEVICE

This application claims priority to Chinese Patent Application Ser. No. CN2016207732715, CN2016207734744, CN2017205472563 and CN2017206064311 filed 21 Jul. 2016, 21 Jul. 2016, 17 May 2017 and 27 May 2017, respectively.

TECHNICAL FIELD OF THE UTILITY MODEL

The present utility model relates to the technical field of medical instruments, and particularly relates to a medical injection device with an adjustable dosage.

BACKGROUND OF THE UTILITY MODEL

As one common medical instrument, an automatic injection device can accurately expel a desired dosage without manual needle insertion, injection and the like.

Patent No. WO2004/078239A1 has disclosed a drug delivery device. The drug delivery device includes: a housing having an internal thread, a dosage dial sleeve having a thread engaged with the internal thread of the housing, a rotary sleeve releasably connected to the dose dial sleeve, and a clutch means located between the dose dial sleeve and the rotary sleeve, wherein, when the dose dial sleeve and the rotary sleeve are coupled, both the sleeves are allowed to rotate with respect to the housing. When the dose dial sleeve and the rotary sleeve are de-coupled, rotation of the dose dial sleeve with respect to the housing is allowed, whilst rotation of the rotary sleeve with respect to the housing is not allowed, whereby axial movement of the rotary sleeve is allowed so that a force is transferred in the longitudinal direction to the proximal end of the drug delivery device. In this drug delivery device, there are many structural parts, and the components have highly required machining precision and great assembly difficulty. For example, a thread matched with a first thread of the piston rod is provided on an inner wall of the rotary sleeve, and a second thread is provided on the piston rod; the second thread and the first thread are arranged reversely; a flexible and helically extending arm is provided on a clicker means in transmission with the clutch means; a toothed member dis provided on the arm in a particular direction; and the like. Moreover, when in use, the internal components easily get stuck or are easily worn out, so that it is likely to result in the failure of the injection device.

Patent No. CN101184521A has disclosed a dosing device. The dosing device is arranged on an injection device or set as a part of the injection device. The dosing device has an adjustment sleeve which is provided at a rear end of the injection device and able to rotate about a longitudinal axis of the injection device, and a rotary sleeve. The rotary sleeve has an external thread which is engaged in the injection device or an internal thread of a housing of the injection device. The rotary sleeve has an internal thread into which an external thread of a locking element is engaged, so that the rotary sleeve is in threaded engagement with the injection device or the housing thereof and in threaded engagement with the locking element. The locking element is borne on a threaded rod in such a manner that it can move in the axial direction but incapable of rotating, and has two opposite guide elements to be engaged into a guide groove extending along the threaded rod in the axial direction, so that the rotation of the threaded rod is always transferred onto the locking element. The locking element rotates with the threaded rod, or in other words, can block rotation of the threaded rod when it is fully screwed into the rotary sleeve, for example. In this injection device, there are many structural parts, and the components have highly required machining precision and great assembly difficulty. For example, ratchet teeth distributed spirally need to be provided on the threaded rod matched with the locking element; threads need to be provided inside and outside of the rotary sleeve; and the like.

Therefore, the injection devices in the prior art are complicated in structure, high in machining difficulty, complicated in assembly, inconvenient in operation and high in manufacturing cost.

SUMMARY OF THE INVENTION

An objective of the present utility model is to provide a medical injection device which is simple in structure, convenient in assembly and low in manufacturing cost.

Another objective of the present utility model is to provide a medical injection device which prevents a piston rod from getting rid of the drive of a driving member when a press operation is performed on an automatic injection device, and thus ensures the stability of transmission.

Another objective of the present utility model is to provide a medical injection device which prevents the drug stored in a vial from being expelled due to misoperation.

To achieve the objectives, the present utility model employs the following technical solutions.

The present utility model provides a medical injection device, including:

a housing having a first end cover and a second end cover provided at two ends thereof, respectively;

a dial threaded rod, which is in threaded connection to the first end cover; and a piston rod, which is used for expelling a dose, an upper end of the piston rod being connected to the dial threaded rod through a driving mechanism while a lower end thereof being in threaded connection to the second end cover;

the medical injection device further includes a dosage adjustment mechanism which is arranged between the dial threaded rod and the housing and used for driving the dial threaded rod to move in an axial direction of the housing; and when the dial threaded rod ascends spirally, the driving mechanism at least partially ascends straightly along with the dial threaded rod; and, when the dial threaded rod descends spirally, the driving mechanism at least partially does a spiral descending motion along with the threaded rod, and drives the piston rod to synchronously do a spiral descending motion.

As a further improvement, the dosage adjustment mechanism includes an adjustment key and a ratchet; the adjustment key is slidingly arranged on the housing and used for driving the ratchet to rotate; and, the ratchet is sheathed on the dial threaded rod and used for driving the dial threaded rod to rotate.

As a further improvement, the ratchet is in torque connection to the dial threaded rod; wherein the adjustment key is sheathed on the dial threaded rod; a protrusion is formed at a lower end of the adjustment key, and a tip portion of the protrusion is fitted onto teeth of the ratchet in the presence of an external force; a strip-shaped through hole arranged in the axial direction of the housing is formed on a side wall of the housing; a bump extending through the strip-shaped through hole is formed on a side wall of the adjustment key; and, when pressed down, the adjustment key is coordinated with the teeth of the ratchet to drive the ratchet to rotate in a single direction, and the dial threaded rod synchronously rotates under the action of the ratchet.

In the technical solutions, the teeth of the ratchet are provided an upper end face of the ratchet, so that the structure is simple and the manufacturing cost is low; by moving the adjustment key up and down to drive the ratchet to rotate in a single direction, the operation is simple and convenient; moreover, different numbers of teeth of the ratchet and different angles of inclination of tooth surfaces may be set according to the requirements for dosage adjustment fineness, so that the dosage is adjusted finely.

As a further improvement, a tension spring for resetting the adjustment key is provided between the upper end of the adjustment key and the first end cover. By connecting the adjustment key to the first end cover through a tension spring, the adjustment key is allowed to automatically restore to the highest point under the action of the tension spring when it is moved to the lowest point, so that it is very convenient to use.

As a further improvement, the driving mechanism includes: a driving member, which is in torque connection to the piston rod; and, an elastic pressing member, which is resisted against a lower end of the driving member and used for maintaining the engagement of the dial threaded rod with the driving member through a ratchet mechanism; when the dial threaded rod ascends spirally, the driving member ascends straightly along with the dial threaded rod under the action of the elastic pressing member, and slides relative to the piston rod; and, when the dial threaded rod descends spirally, the dial threaded rod drives the driving member to rotate through the engagement by the ratchet mechanism, and the piston rod does a spiral descending motion along with the rotation of the driving member.

As a further improvement, the teeth of the ratchet are arranged on a circumferential surface of the ratchet in such a way that the teeth are extended in a circumferential direction of the ratchet; and, the ratchet mechanism includes: teeth arranged on a circumferential surface of the driving member and pawls arranged on an inner wall of the dial threaded rod, the pawls being matched and engaged with the teeth, the direction of inclination of tooth surfaces of the teeth of the ratchet being opposite to that of tooth surfaces of the teeth of the driving member.

As a further improvement, the teeth of the ratchet are arranged on a circumferential surface of the ratchet in such a way that the teeth are extended in a circumferential direction of the ratchet; and, the ratchet mechanism includes: teeth arranged on a circumferential surface of the driving member and pawls arranged on an inner wall of the dial threaded rod, the pawls being matched and engaged with the teeth, the direction of inclination of tooth surfaces of the teeth of the ratchet being opposite to that of tooth surfaces of the teeth of the driving member.

In the technical solutions, by providing an elastic pressing member at the lower end of the driving member, in the process of rotating and extending the dial threaded rod out from the first end cover and under the action of the elastic pressing member, the teeth on the upper end face of the driving member are always fitted to the pawls provided at the lower end of the dial threaded rod; and, when the trigger switch button is pressed down, the piston rod is allowed to synchronously rotate with the dial threaded rod. Furthermore, the amount of the expelled dose is the same as the adjusted dosage, and the fineness of the expelled dosage is improved.

As a further improvement, the medical injection device further includes a vial and a trigger switch button; the vial is arranged at the lower end of the housing, and a piston connected to the piston rod is provided inside the vial; and, the trigger switch button is connected to the upper end of the dial threaded rod.

As a further improvement, the vial is fixed at the lower end of the housing through a vial sleeve; a lower end of the vial sleeve is snapped into the second end cover; and, the second end cover is snapped at the lower end of a cavity of the through hole of the housing.

In the technical solutions, the components are connected integrally in a buckle manner, so it is convenient for assembly.

As a further improvement, a plurality of guide grooves are provided on an inner side wall of the ratchet in an axial direction of the ratchet; the guide grooves are uniformly distributed on a circumferential surface of the ratchet; and, bulges in sliding connection to the guide grooves are formed on an outer wall of the dial threaded rod. By providing guide grooves on an inner side wall of a threaded rod driving cam, and by providing, on the outer wall of the dial threaded rod, bulges in sliding connection to the guide grooves, the fitting of the guide grooves with the bulges forms torque transmission between the dial threaded rod and the threaded rod driving cam, and the bulges slide within the guide grooves when the dial threaded rod is rotated. Moreover, by providing three guide grooves and uniformly distributing the guide grooves on a circumferential surface of the threaded rod driving cam, the structure is simple, the stress is uniform, and it is easier and more convenient to adjust the dosage.

As a further improvement, the driving mechanism includes a first sleeve and a driving member; the first sleeve is sheathed on the piston rod and used for driving the piston rod to rotate; the driving member is arranged within a cavity of the dial threaded rod and resisted against an elastic pressing member arranged above the second end cover, the driving member is used for driving the first sleeve to rotate, and the dial threaded rod and the driving member are engaged with each other through a ratchet mechanism under the pressing of the elastic pressing member; when the dial threaded rod ascends spirally, the driving member ascends straightly under the action of the elastic pressing member; and, when the dial threaded rod descends spirally, the driving member drives the first sleeve to rotate through the engagement by the ratchet mechanism, and the piston rod does a spiral descending motion along with the rotation of the first sleeve.

Since a piston rod, a first sleeve sheathed on the piston rod and a driving member for driving the first sleeve to rotate are provided within a cavity of the dial threaded rod in the transmission structure, under the compression of the elastic pressing member, the dial threaded rod and the driving member may be always engaged with each other through a ratchet mechanism, so that the flexible connection is maintained. Meanwhile, when the dial threaded rod ascends spirally, the driving member may ascend straightly under the action of the elastic pressing member and may slide relative to the first sleeve. Therefore, when the dial threaded rod descends spirally, the driving member may be driven by the dial threaded rod through the engagement by the ratchet mechanism, and may drive the first sleeve to rotate while doing a spiral descending motion, so that the rotation of the piston rod along with the first sleeve is ensured. The piston rod is allowed to do a spiral descending motion by virtue of the threaded match with the second end cover. Thus, in the case where the length of the first sleeve satisfies the design requirements, the disconnection of the piston rod from the first sleeve during the rotation is avoided to the largest degree, so that the piston rod is prevented from getting rid of the drive of the driving member, and the continuous rotation of the piston rod is realized. Furthermore, medicine liquid in the vial is expelled according to the scale displayed on the dial threaded rod, so it is ensured that the dosage in the automatic injection device can be utilized fully, and the stability of the transmission process is maintained.

As a further improvement, the driving member is a second sleeve sheathed on the first sleeve, wherein the second sleeve is in sliding connection to an upper end of the first sleeve, and the second sleeve slides in an axial direction of the dial threaded rod when the dial threaded rod ascends spirally.

As a further improvement, a boss is provided at an upper end of the second sleeve; and a neck matched with the boss is provided at an upper end of the first sleeve, wherein, when the dial threaded rod ascends spirally, the boss slides upward within the neck; and, when the dial threaded rod descends spirally, the boss slides downward within the neck and drives the second sleeve to rotate.

As a further improvement, the maximum displacement of a relative slip generated between the boss and the neck is less than or equal to the length of external threads on the dial threaded rod.

As a further improvement, the piston rod includes: a driving portion arranged within a cavity of the first sleeve, and a threaded segment connected to the driving portion, wherein the section of the driving portion is matched in shape and size with the section of the cavity of the first sleeve; and the driving portion synchronously rotates when the first sleeve rotates, and is fitted with threads of the second end cover through the threaded segment.

As a further improvement, the ratchet mechanism includes: first teeth provided on the top of the cavity of the dial threaded rod, and second teeth provided on the top of the second sleeve and fitted with the first teeth, wherein both the first teeth and the second teeth are distributed circumferentially.

As a further improvement, a first resisting portion and a second resisting portion used for resisting against the elastic pressing member are provided at the lower end of the first sleeve and the lower end of the second sleeve, respectively, wherein the elastic pressing member is arranged between the first resisting portion and the second resisting portion, and the first resisting portion and the second resisting portion are always resisted against the elastic pressing member.

As a further improvement, the medical injection device further includes: a cap which is arranged within a through hole of the first end cover and buckled with the upper end of the dial threaded rod, and a gland arranged on the cap, wherein a fixed shaft is provided in a center of the gland, and the fixed shaft is inserted into the cavity of the dial threaded rod through a hollow portion of the cap.

As a further improvement, a convex ring used for contacting and pressing the cap is provided on the top of an inner surface of the gland.

As a further improvement, the second end cover and the housing are formed integrally, and an end face of the second end cover is resisted against the bottom of the first sleeve.

As a further improvement, the dosage adjustment mechanism includes: a ratchet for driving the dial threaded rod to rotate, and a key which is slidingly provided on the first end cover and used for driving the ratchet to rotate; and, at least part of the key is an elastic component used for being inserted into a socket of a tooth of the ratchet, wherein the teeth of the ratchet are distributed about an axis of the ratchet; after the key is pressed down, the elastic component touches the teeth to generate elastic deformation, slides into the socket of the tooth, and pushes the ratchet to rotate; and, the elastic component can be restored to an initial shape after the key is released, and can slide into a socket of a tooth adjacent to the tooth to push the ratchet to rotate in a single direction after the key is pressed down again.

As a further improvement, a surface of each tooth is obliquely extended from an inner side to an outer side of the ratchet, and the top of each tooth is located between a top end and a bottom end of an adjacent tooth, wherein, when the key is pressed down, the elastic component slides from the top end to the bottom end of a corresponding tooth along the surface of this tooth, and then pushes the ratchet to rotate.

As a further improvement, at least parts of the surfaces of the teeth of the ratchet are spiral surfaces, or the surfaces of the teeth of the ratchet are oblique planes.

As a further improvement, a limiting groove for limiting the elastic component is formed on a back of each tooth, and each limiting groove is located at a position where the respective tooth back is connected to the bottom end of an adjacent tooth.

As a further improvement, the medical injection device further includes a compression spring which is provided within the housing and used for compressing the key, and the compression spring compresses the key toward an initial position to separate from the corresponding tooth after the key is released; wherein the scalable length of the pressing spring is greater than or equal to a distance from the top end to the bottom end of the corresponding tooth in an axial direction of the ratchet.

As a further improvement, the elastic component includes a bent segment and a vertical segment connected to the bent segment, and the vertical segment is parallel to the axial direction of the ratchet.

As a further improvement, a portion of the vertical segment facing the ratchet is a curved surface, and the width of the vertical segment gradually decreases from one end thereof connected to the bent segment to its bottom end.

As a further improvement, the key includes: a connector connected to the elastic component, and a key body in snap-in connection to the connector, with the connector being resisted against the compression spring.

As a further improvement, the key structure further includes an end cover; a groove for accommodating the connector is formed on the end cover; and the length of the groove is greater than that of the connector.

As a further improvement, the medical injection device further includes a protection mechanism for limiting the rotation of the ratchet, the protection mechanism includes a safety switch and a locking mechanism, and the locking mechanism is locking teeth arranged on a circumferential surface of the ratchet; and, the safety switch is rotatably arranged within a mounting hole on a side wall of the housing, so that a latch of the safety switch is engaged with or disengaged from the locking teeth after the safety switch is rotated.

In the technical solutions, by limiting the inverse rotation of the ratchet through the protection mechanism, the inverse rotation of the dial threaded rod is effectively prevented from driving the piston rod to rotate, it is ensured that the dosage will not be reduced due to the inverse rotation of the ratchet after the dosage is adjusted, and it is prevented that the medicine is expelled and thus wasted after the trigger switch is touched unconsciously. Accordingly, the safety of the medicine is improved, the structure is simple, and it is easy to operate.

As a further improvement, the safety switch is snapped in the mounting hole on the side wall of the housing through a hasp.

As a further improvement, the medical injection device further includes a needle shield and a shield resetting member; the vial is fixed at the lower end of the housing through a vial sleeve; an upper end of the vial sleeve is snapped in the second end cover, and the needle shield can slide relative to a wall of an inner cavity of the vial sleeve and is embedded at an lower end of the inner cavity of the vial sleeve; and, the shield resetting member is arranged between the needle shield and the wall of the inner cavity of the vial sleeve, and used for extruding the needle shield into the vial sleeve in the presence of an external force and urging the needle shield to extend out from the vial sleeve after the external force is released.

In the technical solutions, under the action of the shield resetting member, the needle shield covers the needle therein so as to protect the needle and prevent the needle from pricking others.

As a further improvement, the second end cover is snapped at the lower end of the cavity of the through hole of the housing.

With the technical solutions, the present utility model have the following beneficial effects:

compared with the prior art, the medical injection device of the present utility model has the advantages of simple structure, easy adjustment, high adjustment fineness, high safety coefficient, easy operation, low manufacturing cost and the like.

DETAILED DESCRIPTION OF THE INVENTION

Figure 1:
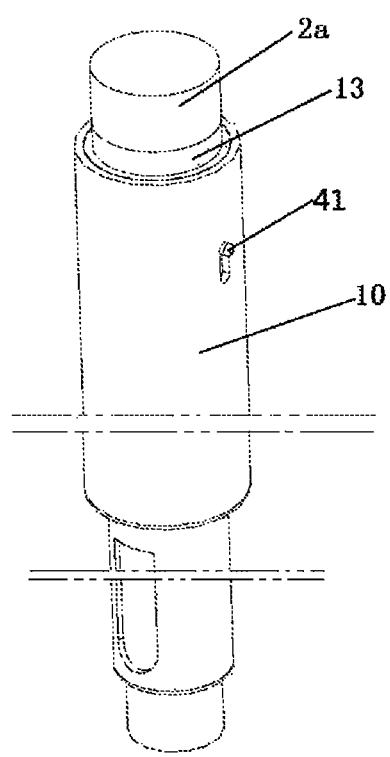
FIG. 1 is a structure diagram of a medical injection device according to Embodiment 1 of the present utility model.

The technical solutions in the embodiments of the present utility model will be clearly and completely described below with reference to the accompanying drawings in the embodiments of the present utility model. Apparently, the embodiments described herein are merely a part but not all of the embodiments of the present utility model. All other embodiments obtained by a person of ordinary skill in the art without paying any creative effort on the basis of the embodiments in the present utility model shall fall into the protection scope of the present utility model.

Embodiment 1

As shown in FIGS. 1 to 7, Embodiment 1 of the present utility model provides a medical injection device with an adjustable dosage, including a housing 10, a vial which is provided at one end of an inner cavity of a through hole of the housing 10 and has a piston 34, a trigger switch button 2a, a piston rod 21, a dial threaded rod 9, a dosage adjustment mechanism arranged within the housing 10, and a driving mechanism, wherein a first end cover 13 is provided at an upper end of the housing 10, while a second end cover 19 is provided a lower end thereof; the second end cover 12 is snapped at a lower end of a cavity of a through hole of the housing 10; and, through holes are formed in both the middle of the first end cover 13 and the middle of the second end cover 19. The vial is fixed at a lower end of the housing 10 through a vial sleeve, and an upper end of the vial sleeve is snapped into the second end cover 19. The dose dosage adjustment mechanism includes an adjustment key 4a and a ratchet 2. The ratchet 2 is embedded into the cavities of the through holes of the housing 10. The ratchet 2 is sheathed on the dial threaded rod 9 and is in torque connection to the dial threaded rod, so that the both can slide relative to each other in the axial direction. It is to be noted that, the torque connection described in the present utility model means that one of two interconnected objects or components drives the other object or component to rotate. In this embodiment, guide grooves are provided on an inner side wall of the ratchet 2 in the axial direction, and bulges in sliding connection to the grooves are provided an outer wall of the dial threaded rod 9. By fitting the guide grooves with the bulges, torque transmission is formed between the dial threaded rod 9 and the ratchet 2, and the bugles slide within the guide grooves when the ratchet 2 and the dial threaded rod 9 are rotated. To realize uniform stress and smooth adjustment, there are three guide grooves uniformly distributed on a circumferential surface of the ratchet 2. A tooth surface of the ratchet 2 is connected to the adjustment key 4a, and the ratchet 2 is driven to rotate in a single direction by driving the adjustment key 4a. External threads are provided on the outer wall of the dial threaded rod 9. The external threads are in fitted connection to internal threads on the through hole in the middle of the first end cover 13. An upper end of the dial threaded rod 9 is connected to the trigger switch button 2a, while a lower end thereof is connected to a driving member 71. A lower end of the driving member 71 is connected to the piston rod 21 in a torque transmission manner. Specifically, the driving member 71 is sheathed on a square rod at the upper end of the piston rod 21 to transfer torque. External threads are provided on an outer wall of the piston rod 21, and the external threads are in fitted connection to internal threads on the through hole in the middle of the second end cover 19.

Wherein, a circle of first ratchets having upward tooth surfaces are formed on an upper end face of the driving member 71 along the circumference of the driving member 71, and pawls 62 matched with the first ratchets are provided on the dial threaded rod 9. In this embodiment, the dial threaded rod 9 is sheathed on the piston rod 21; upper ends of both the driving member 21 and the piston rod 21 are located within a cavity of the dial threaded rod 9; the pawls 62 are provided on a top wall of the cavity of the dial threaded rod 9; and, a compression spring 72 used for allowing the first ratchets at the upper end of the driving member 71 and the pawls on the top wall of the cavity of the dial threaded rod 9 to be always engaged with each other is provided between the lower end of the driving member 71 and the second end cover 19. When the trigger switch button 2a is pressed down to drive the dial threaded rod 9 to descend spirally after the dosage is adjusted, due to the engagement of the first ratchets with the pawls 62, the piston rod 21 will simultaneously rotate, so that the adjusted dosage is ensured to be the same as the amount of the expelled and injected dose.

As a preferred implementation of the present utility model, the teeth of the ratchet 2 are arranged on an upper end face of the ratchet 2 in such a way that the teeth are extended in a circumferential direction of the ratchet 2, wherein the direction of inclination of tooth surfaces of the ratchet 2 is the same as that of tooth surfaces of the first ratchets.

The adjustment key 4a is sheathed on the dial threaded rod 9. A protrusion 42 is formed at a lower end of the adjustment key 4a, and a tip portion of the protrusion 42 may be fitted onto a tooth surface of the ratchet 2 in the presence of an external force. A strip-shaped through hole arranged in the axial direction of the housing 10 is formed on a side wall of the housing 10. A bump 4141 extending through the strip-shaped through hole is formed on a side wall of the adjustment key 4a. The bump 41 is extended to an outer side of the housing 10. The bump 41 is convenient for a finger of a user to apply an external force to the bump, so as to drive the adjustment key 4a to move in the axial direction of the housing 10 as a whole. Of course, other structures convenient for driving the adjustment key 4a to move may also be used to replace the bump 41. For the convenience of operation, a tension spring 43 is provided between the upper end of the adjustment key 4a and the first end cover 13. When the adjustment key 4a is moved to the lowest position of the strip-shaped through hole and after the external force is released, under the action of the tension spring 43, the adjustment key 4a may automatically restore to the highest point of the strip-shaped through hole to get ready for the next adjustment.

In an initial state, the lower end of the trigger switch button 2a is fitted with the upper end of the housing 10, and the piston rod 21, together with the piston 34, is located at the highest position of the vial. Thus, during the operation, the user may drive the ratchet to rotate in a single direction by the adjustment key according to the amount of the dose to be injected every time, so that the dial threaded rod realizes synchronous rotation with the ratchet 2 by virtue of the fitted connection of the external threads arranged on the outer wall of the dial threaded rod and the internal threads arranged on the through hole of the first end cover. When the ratchet 2 is rotated by a certain angle, the dial threaded rod 9 is extended outward a certain displacement relative to the first end cover 13. This displacement is embodied by the scale on the surface of the dial threaded rod 9. When the user has adjusted the scale and then pressed down the trigger switch button 2a, the dial threaded rod 9 is driven to rotate in an opposite direction until the lower end of the trigger switch button 2a is fitted to the upper end of the housing 10 again. In this way, the injection of the adjusted dosage is completed, and the dose is prevented from being expelled in an excessive amount. In this case, the dial threaded rod 9 is retracted into the first end cover 13.

The working principle of this embodiment is as follows.

The adjustment key 4a is driven to move down, and the protrusion 42 of the adjustment key 4a is resisted against a tooth surface at the upper end of the ratchet 2 to drive the ratchet 2 to rotate in a single direction. The dial threaded rod 9 synchronously rotates with the ratchet 2 under the action of the bulges and the guide grooves. The external threads arranged on the outer wall of the dial threaded rod 9 are in fitted connection to the internal threads arranged on the through hole of the first end cover 13. After the ratchet 2 is rotated by a certain angle, the dial threaded rod 9 is extended outward a certain displacement relative to the first end cover 13. This displacement is embodied by the scale on the surface of the dial threaded rod 9. After the scale is adjusted, the trigger switch button 2a is pressed down. The trigger switch button 2a drives the dial threaded rod 9 to rotate in an opposite direction and spirally descend to retract into the first end cover 13. The pawls 62 of the dial threaded rod 9 are engaged with the first ratchets on the upper end face of the driving member 71, so that the piston rod 21 is driven to rotate synchronously. Since the external threads arranged on the outer wall of the piston rod 21 are in fitted connection to the internal threads arranged on the through hole of the second end cover 19, the piston rod 21 drives the piston 34 to move down relative to the vial, so that the medicine liquid at the adjusted dosage is expelled.

Figure 7:
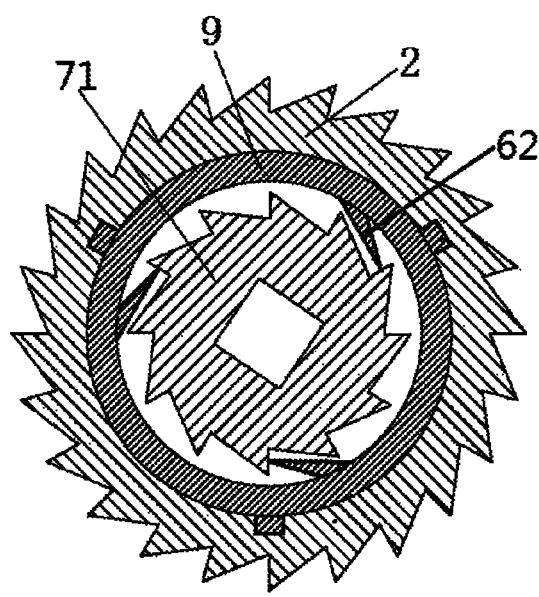
FIG. 7 is a structure diagram of a ratchet and a driving mechanism in another form according to Embodiment 1 of the present utility model.

As shown in FIG. 7, in this embodiment, the teeth of the ratchet 2 are arranged on a circumferential surface of the ratchet 2 in such a way that the teeth are extended in a circumferential direction of the ratchet 2; a strip-shaped through hole extending in a circumferential direction the housing 10 is provided on the housing 10 at a position corresponding to the teeth of the ratchet 2; a bump extending through the strip-shaped through hole is formed on the side wall of the adjustment key 4a; pawls engaged with the teeth of the ratchet 2 are formed on the inner wall of the adjustment key 4a; second ratchets are provided on a circumferential surface of the driving member 71; and, pawls 62 fitted with the second ratchets are provided on the inner wall of the dial threaded rod 9, wherein the direction of inclination of tooth surfaces of the ratchet 2 is opposite to that of tooth surfaces of the second ratchets.

Embodiment 2

As shown FIGS. 8 to 19, Embodiment 1 of the present utility model provides another medical injection device. This medical injection device mainly consists of a housing 10, a dial threaded rod 9 provided within the housing 10 and having a cavity, a first end cover 13 and a second end cover 19 respectively provided at an upper end and a lower end of the housing 10, a piston rod 21 used for expelling medicine liquid, a first sleeve 20 sheathed on the piston rod 21 and used for driving the piston rod to rotate, a driving member arranged within the cavity of the dial threaded rod 9 and used for driving the first sleeve 20 to rotate, and an elastic pressing member arranged above the second end cover 19 and resisted against the driving member.

Figure 12:
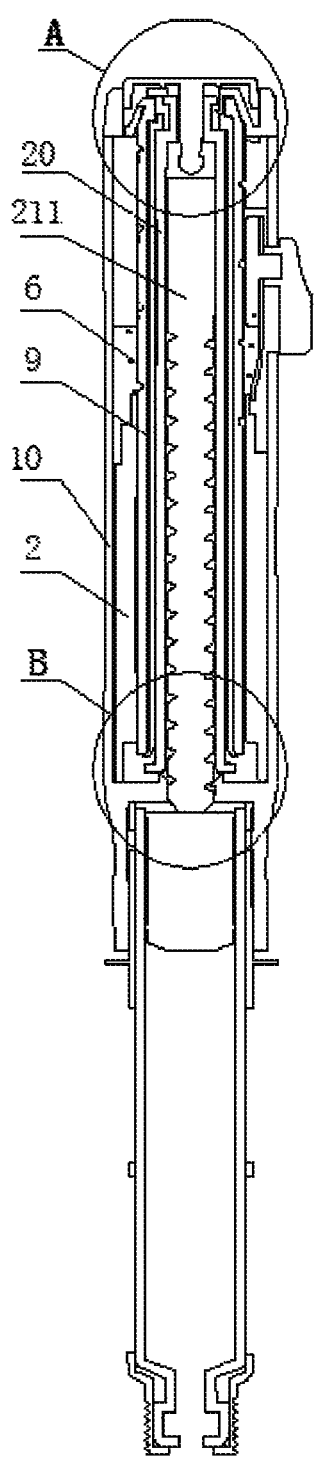
FIG. 12 is a cross-sectional view of the interior according to Embodiment 2 of the present utility model.
Figure 14:
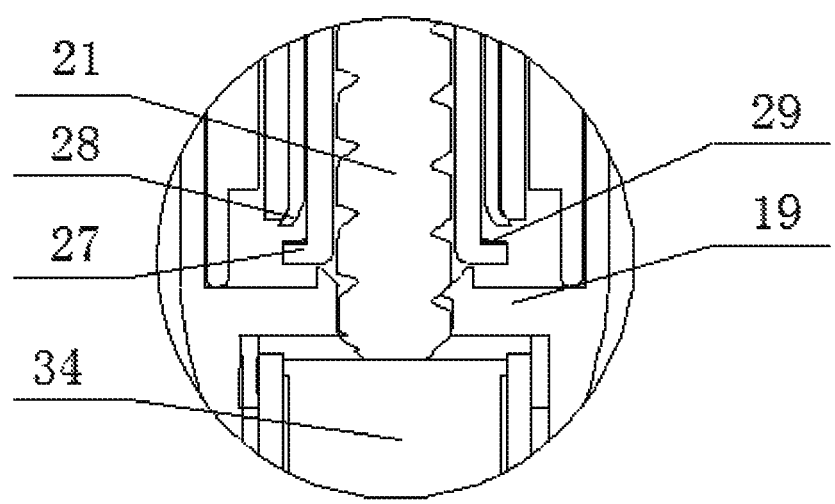
FIG. 14 is a partially enlarged view of B of FIG. 12.

Wherein, preferably, to satisfy the design and assembly requirements in practical applications, optimize processes and save the cost, as shown in FIGS. 12 and 14, the second end cover 19 and the housing 10 are formed integrally, and an end face of the second end cover 19 is resisted against the bottom of the first sleeve 20. The upper end of the dial threaded rod 9 is in threaded connection to the first end cover 13. The piston rod 21 passes through the through hole of the second end cover 19, and in fitted connection to internal threads on an inner wall of this through hole. And, in practical operations, when the dial threaded rod 9 is rotated in the presence of an external force and ascends spirally under the coordination of the first end cover 13, the driving member does a straight ascending motion under the compression of the elastic pressing member and is always engaged with the dial threaded rod 9 through a ratchet mechanism, without mutual rotation. When the dial threaded rod 9 descends spirally, under the compression of the elastic pressing member, the driving member drives the first rotate sleeve 20 to rotate through the engagement by the ratchet mechanism; and the piston rod 20 does a spiral descending motion along with the rotation of the first sleeve 20 when the first sleeve 20 rotates.

As described above, since a piston rod 21, a first sleeve 20 sheathed on the piston rod 21 and a driving member for driving the first sleeve 20 to rotate are provided within a cavity of the dial threaded rod 9 in the medical injection device, under the compression of the elastic pressing member, the dial threaded rod 9 and the driving member may be always engaged with each other through a ratchet mechanism, so that the flexible connection is maintained. Meanwhile, when the dial threaded rod 9 ascends spirally under the action of the first end cover, the driving member may ascend straightly under the action of the elastic pressing member and may slide relative to the first sleeve 20. Therefore, when the dial threaded rod 9 descends spirally, the driving member may be driven by the dial threaded rod 9 through the engagement by the ratchet mechanism, and may drive the first sleeve 20 to rotate while doing a spiral descending motion, so that the rotation of the piston rod 21 along with the first sleeve 20 is ensured. The piston rod is allowed to do a spiral descending motion by virtue of the threaded match with the second end cover 19. Thus, in the case where the length of the first sleeve 20 satisfies the design requirements, the disconnection of the piston rod 21 from the first sleeve 20 during the rotation is avoided to the largest degree, so that the piston rod 21 is prevented from getting rid of the drive of the driving member, and the continuous rotation of the piston rod 21 is realized. Furthermore, since medicine liquid in the vial (not shown) is expelled according to the scale displayed on the dial threaded rod 9, so it is ensured that the dosage in the automatic injection device can be utilized fully, and the stability of the transmission process is maintained.

Figure 10:
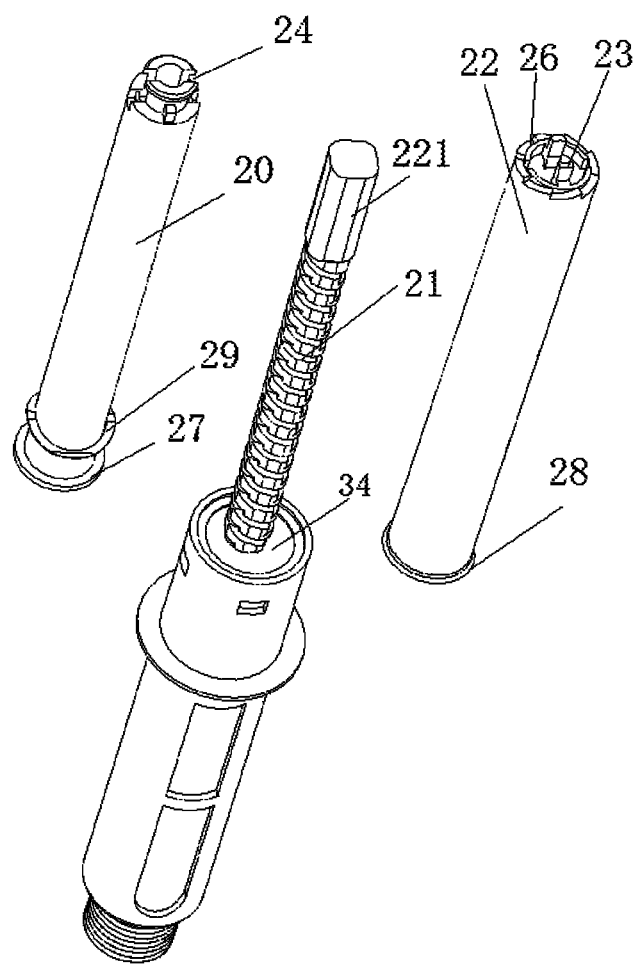
FIG. 10 is a diagram showing parts inside the dial threaded rod according to Embodiment 2 of the present utility model.
Figure 11:
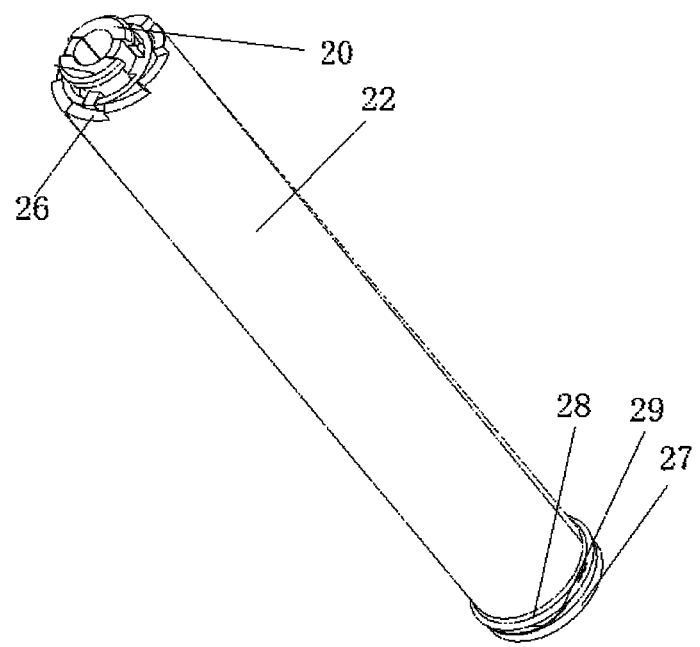
FIG. 11 is a schematic diagram of assembling a first sleeve and a second sleeve according to Embodiment 2 of the present utility model.

Specifically, as shown in FIGS. 10 and 11, to satisfy the design and assembly requirements in practical applications, the driving member is a second sleeve 22 sheathed on the first sleeve 20, and the first sleeve 20 is in sliding connection to an upper end of the second sleeve 20. Thus, through the fitting of the first sleeve 20 with the second sleeve 22, during the spirally ascending of the dial threaded rod 9, the sliding of the second sleeve 20 in the axial direction of the dial threaded rod 9 will not drive the first sleeve 20 to rotate.

As shown in FIG. 10, the piston rod 21 mainly consists of a driving portion 211 and a threaded segment (not shown) connected to the driving portion 211, and the section of the driving portion 211 is matched in shape and size with the section of the cavity of the second sleeve 22. The driving portion 211 performs synchronous rotation when the first sleeve 20 rotates, and is fitted with threads of the second end cover 19 through the threaded segment of the piston rod 21. Thus, a torque may be formed with the cavity of the first sleeve 20 through the driving portion 21 of the piston rod 21, and the synchronous rotation of the piston rod 21 and the first sleeve 20 is realized. Meanwhile, due to the fitted connection to the threads of the second end cover 19, the driving portion 211 is allowed to slide in the axial direction of the cavity of the first sleeve 20 and move down according to the ascending distance of the dial threaded rod 9, so that the driving portion 211 is moved toward one side of the vial and thus difficult to separate from the first sleeve 20. Moreover, it is to be noted that, preferably, the section of the driving portion 211 of the piston rod 21 is rectangular in this embodiment; while in practical applications, the section may be hexagonal, octagonal or in other polygons. Therefore, the specific shape and size of the section will not be specifically limited or excessively stated in this embodiment.

Further, as shown in FIG. 11, a boss 23 is provided at an upper end of the second sleeve 22; and correspondingly, a neck 24 matched with the boss 23 is provided at an upper end of the first sleeve 20, wherein, when the dial threaded rod 9 ascends spirally, the boss 23 slides upward within the neck 24.

Further, in the practical design process, when the dial threaded rod 9 descends spirally, the boss 23 of the second sleeve 22 slides downward within the neck 24 of the first sleeve 20 and drives the first sleeve 20 to rotate. Thus, through the sliding of the boss 23 of the second sleeve 22 within the neck 24 of the second sleeve, the first sleeve 20 is allowed to stably slide in the axial direction when the dial threaded rod 9 ascends spirally; and, when the first sleeve 20 descends spirally along with the dial threaded rod 9, through the fitting of the boss 23 with the neck 24, a torque is generated to the first sleeve 20, and the first sleeve 20 is thus driven to synchronously rotate, so that the stability of transmission is ensured.

Figure 8:
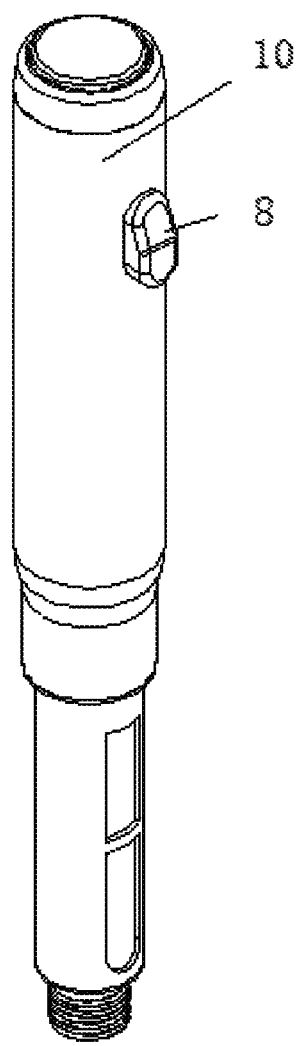
FIG. 8 is an external structure diagram of a medical injection device according to Embodiment 2 of the present utility model.

As shown in FIG. 8, the boss 23 consists of a plurality of boss members which are provided on the top of the cavity of the second sleeve 22 and extended upward in the axial direction. And, in this embodiment, there are preferably two boss members symmetrically arranged on the top of the second sleeve 22. Each of the boss members consists of a horizontal segment (not shown) and a vertical segment (not shown), and the horizontal segment is connected to the top of the cavity of the second sleeve 22. Correspondingly, on the top of the cavity of the first sleeve 20, an opening partially extending upward and passing through the top of the cavity of the second sleeve 22 is formed, and a snap-in portion (not shown) with a neck 24 is formed.

To prevent the disconnection of the first sleeve 20 from the second sleeve 220 during sliding relative to each other, in the practical design and application process, preferably, the maximum displacement of a relative slip generated between the boss 23 and the neck 24 (i.e., the relative displacement between the first sleeve 20 and the second sleeve 22) needs to be less than the length of the external threads on the dial threaded rod 9 (i.e., a distance between a starting segment and an ending segment of the external threads in the axial direction of the dial threaded rod 9, which is equivalent to the maximum ascending distance of the dial threaded rod 9). Apparently, this relative displacement may also be equal to the length of the external threads on the dial threaded rod 9. This will not be excessively or briefly stated in this embodiment.

In addition, in this embodiment, preferably, as shown in FIGS. 10 and 12, the ratchet structure mainly consists of a plurality of teeth 25 arranged on an inner wall of the top of the cavity of the dial threaded rod 9, and a plurality of teeth 26 arranged on the second sleeve 22 and matched with the teeth 25, wherein the teeth 25 and the teeth 26 are circumferentially distributed on the top of the cavity of the dial threaded rod 9 and on the top of the second sleeve 22, respectively. Thus, it is ensured that the dial threaded rod 9 can smoothly drive the second sleeve 2 to rotate and slide downward in the axial direction of the dial threaded rod 9 only when the dial threaded rod 9 descends spirally.

Meanwhile, as shown in FIG. 10, a first resisting portion 27 and a second resisting portion 28 used for resisting against the elastic pressing member are provided at the lower end of the first sleeve 20 and the lower end of the second sleeve 22, respectively. Wherein, the elastic pressing member is arranged between the first resisting portion 27 and the second resisting portion 28, and the first resisting portion 27 and the second resisting portion 28 are always resisted against the elastic pressing member. By means of the first resisting portion 27 and the second resisting portion 28, the first sleeve 20 and the second sleeve 22 can be better resisted against the elastic pressing member, and it is ensured that, under the action of the elastic pressing member, the teeth 26 of the second sleeve 22 can be better engaged with the teeth 25 on the dial threaded rod 9.

Preferably, as shown in FIG. 10, the elastic pressing member is a metal shrapnel 29 which is sheathed on the first sleeve 20 and resisted against the second sleeve 22. Since the metal shrapnel 29 is good in rebound resilience, high in durability and not easy to result in failure, the stability of the medical injection device may be improved.

In addition, to satisfy the design requirements in practical applications, a first resisting portion 27 and a second resisting portion 28 used for resisting against the metal shrapnel 29 are provided at the lower end of the first sleeve 20 and the lower end of the second sleeve 22, respectively. Wherein, the metal shrapnel 29 is sheathed on the second sleeve 22 and resisted against the first resisting portion 27 and the second resisting portion 28. Apparently, in this embodiment, the elastic pressing member may also be replaced with elastic elements such as a spring. Therefore, what kind of elastic element used as the elastic pressing member will not be specifically limited or stated excessively.

Specifically, as shown in FIGS. 10 and 14, the metal shrapnel 29 includes a hollow portion (not shown) sheathed on the second sleeve 22, and a bent portion (not shown) connected to the hollow portion. And, at least part of the body portion is fitted to an end face of the first resisting portion 27, and at least part of the bent portion is fitted to an end face of the second resisting portion 28, to increase the contact area of the metal shrapnel 29 with the first sleeve 20 and with the second sleeve 22.

In addition, in this embodiment, to be convenient for the user's operation and use, the medical injection device further includes: a cap 30 which is arranged within the through hole of the first end cover 13 and buckled with the upper end of the dial threaded rod 9, and a gland 31 arranged on the cap 30. Wherein, a fixed shaft 32 is provided in a center of the gland 31; the fixed shaft 32 is inserted into the cavity of the dial threaded rod 9 through a hollow portion of the cap 30; and a center axis of the fixed shaft 32 is coincided with a center axis of the dial threaded rod 9. Thus, after the user presses down the gland, the cap 30 drives the dial threaded rod 9 to move down under the action of the gland 31, and then rotates about the fixed shaft 32 as a center axis so as to drive the second sleeve 22 to rotate. Meanwhile, since the fixed shaft 32 is inserted into the cavity of the dial threaded rod 9 through the hollow portion of the cap 30, in practical applications, it is convenient to assemble and position the gland 31, the cap 30 and the dial threaded rod 9.

Figure 13:
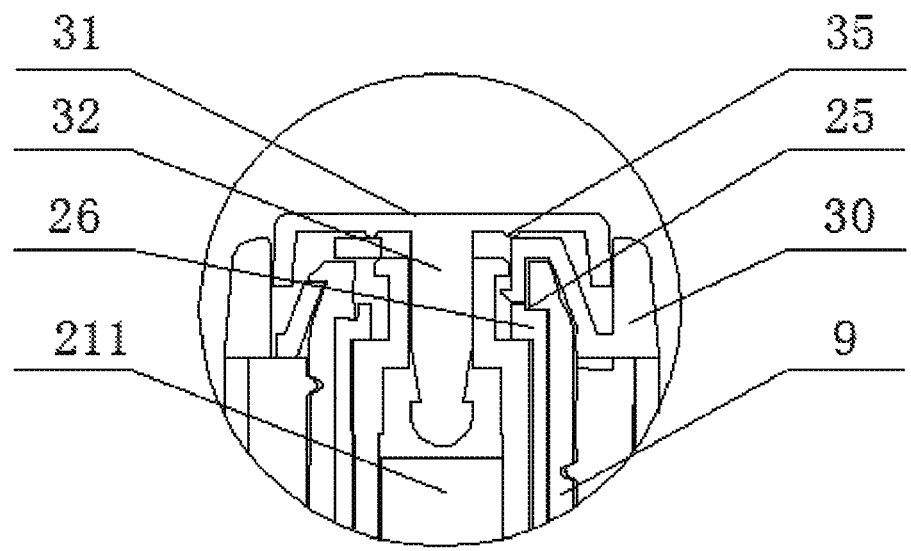
FIG. 13 is a partially enlarged view of A of FIG. 12.

Further, as shown in FIG. 13, a convex ring 35 is provided on the top of an inner surface of the gland 31, and the convex ring 35 is used for contacting and pressing the cap 30 by using the fixed shaft 32 as a center. Thus, through the contact of the convex ring 35 with the cap 30, the contact area of the gland 31 with the cap 30 may be decreased, and an acting force between the gland 31 and the cap 30 is thus increased. As a result, when the gland 31 is pressed down, the gland 31 can smoothly press down the cap 30 and allow the cap 30 to do a spiral descending motion.

It is to be noted that, to prevent the fixed shaft 32 from contacting with the second sleeve 22 when the gland 31 is pressed down, after the boss 23 is buckled with the neck 24, a cavity for allowing the fixed shaft 32 to be inserted therein is also formed, and this cavity is communicated with the cavity of the first sleeve 20.

Meanwhile, as shown in FIG. 14, to allow the dial threaded rod 9 to ascend stably under the drive of the ratchet 2 and by virtue of the threaded connection to the first end cover 13, preferably, a groove 33 for fixing the first end cover 13 is further provided on the side wall of the cavity of the housing 10, and a buckling member (not shown) buckled with the groove 33 is also provided on the first end cover 13, so that it is convenient to connect the first end cover 13 to the housing 10 in an interference fit manner. Apparently, the connection may also be realized by gluing, threaded connection or snap-joint in this embodiment. This will not be specifically limited or described in this embodiment.

Figure 15:
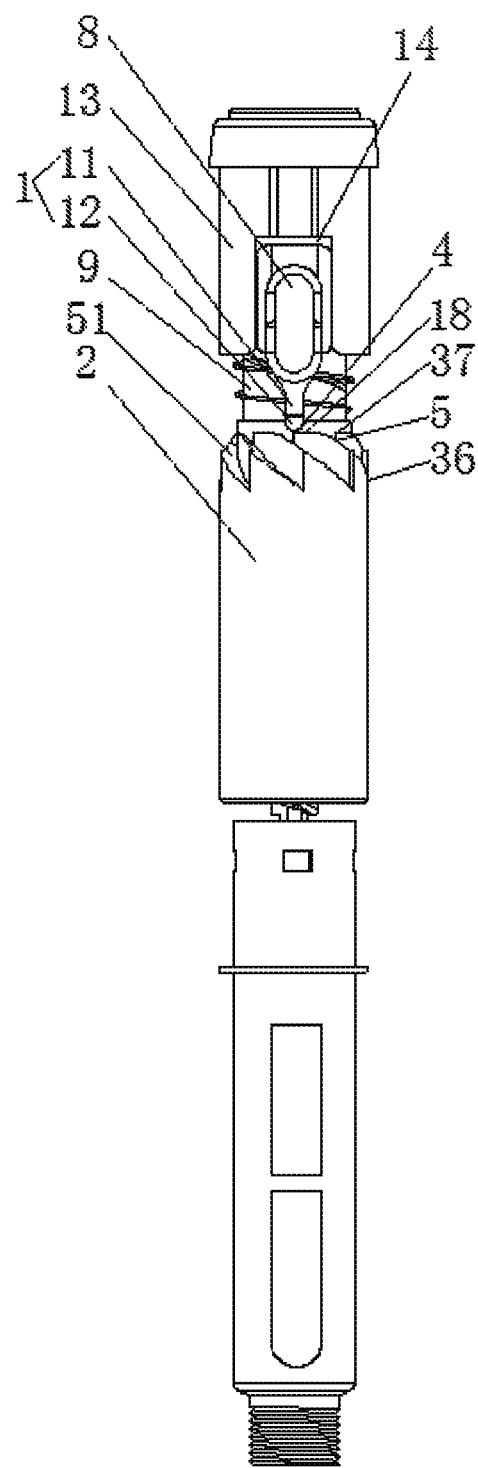
FIG. 15 is a structure diagram of the interior of a housing according to Embodiment 2 of the present utility model.
Figure 16:
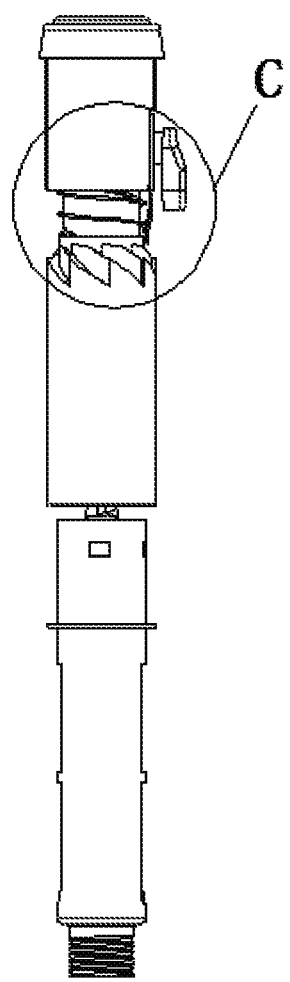
FIG. 16 is a side view of the interior of the housing according to Embodiment 2 of the present utility model.
Figure 17:
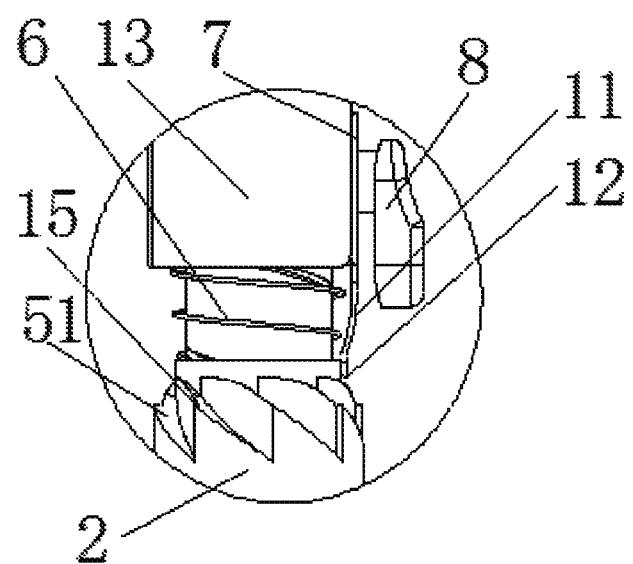
FIG. 17 is a partially enlarged view of C of FIG. 16.

Specifically, in this embodiment, as shown in FIGS. 16 and 17, the medical injection device further includes: a ratchet 2 which is sheathed on the dial threaded rod 9 and used for driving the dial threaded rod 9 to rotate, and a key which is slidingly provided on the first end cover and used for driving the ratchet 2 to rotate. Further, an elastic component 1 used for being inserted into a socket of a tooth 5 of the ratchet 2 is provided on the key. Wherein, as shown in FIG. 15, after the key is pressed down, the elastic component 1 touches the tooth 5 of the ratchet 2 directly facing the key to generate elastic deformation, slides into the socket of the tooth 5, and pushes the ratchet 2 to rotate. The elastic component 1 can restore to an initial shape after the key is released, and can slide into a socket of a tooth adjacent to the tooth 5 after the key is pressed down again. By performing this reciprocated operation, the ratchet 2 is pushed to rotate in a single direction.

As described above, since the key in the key structure has an elastic component 1 capable of being inserted into a socket of a tooth of the ratchet, and the elastic component 1 may be pressed toward a corresponding tooth 5 of the ratchet 2 by pressing the key in practical operations, by virtue of the elastic deformation generated by the elastic component 1 when touching the tooth 5, the elastic component 1 is allowed to smoothly slide into the socket of the tooth 5 and push the ratchet 2 to rotate. After the user releases the key, the elastic component 1 may restore to the initial shape, so that the elastic component is inserted into a socket of the next tooth to push the ratchet 2 to rotate in a single direction after the user presses down the key again. Consequently, the key may be prevented from getting stuck in the process of pushing the ratchet 2 to rotate, the user can smoothly and continuously press down the key to realize the continuous rotation of the ratchet, and the reliability and the stability of the key structure are thus ensured. Moreover, the key is simple in structure and tactful in design, and the production cost may be reduced greatly.

Figure 9:
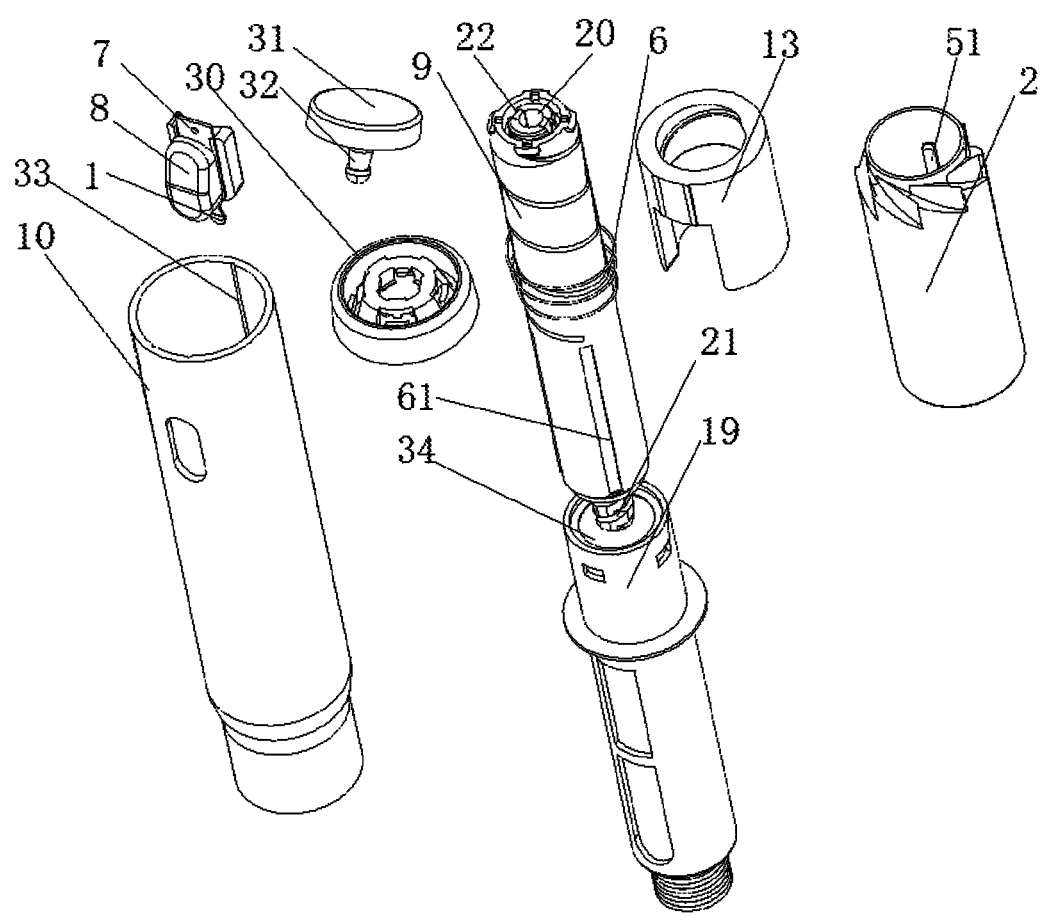
FIG. 9 is an exploded view of the medical injection device according to Embodiment 2 of the present utility model.

Further, it is to be noted that, in this embodiment, as shown in FIGS. 9, 10 and 12, when the ratchet 2 rotates clockwise, the external threads on the dial threaded rod 9 and the internal threads in the through hole of the first end cover 13 are left-band threads; and correspondingly, when the teeth 5 on the second sleeve 22 rotates counterclockwise when the dial threaded rod descends spirally, the threaded segment of the piston rod 21 and the internal threads in the through hole of the second end cover 19 are left-band threads. Further, it is ensured that, once the user presses down the gland 31, the descending distance of the piston rod 21 during every press is equal to the ascending distance of the dial threaded rod 9 during the adjustment before every press. Similarly, when the ratchet 2 rotates counterclockwise, the threads of the components may also be designed as right-hand threads. Therefore, the direction of rotation of each component and the design of the threads as left-hand threads or right-hand threads will not be specifically limited in this embodiment.

Specifically, to satisfy the design and assembly requirements in practical applications, as shown in FIGS. 16 and 17, the elastic component 1 mainly consists of a bent segment 11 and a vertical segment 12 connected to the bent segment 11, and the vertical segment 12 is parallel to the axial direction of the ratchet 2. With such a structural design, it may be convenient for an operator to mount the key according to the internal structure of the automatic injection device, and the vertical segment 12 can better apply an acting force to a tooth surface 51 of a tooth 5 in the axial direction of the ratchet 2 after the user presses the key down.

Further, a portion of the vertical segment 12 facing the ratchet 2 is a curved surface 4, and the width of the vertical segment 12 gradually decreases from one end thereof connected to the bent segment 11 to its bottom end. Thus, by virtue of the curved surface 4, after the vertical segment 12 touches a tooth 5, the resistance to the vertical segment 12 may be decreased, so that the vertical segment 12 can slide into the socket of the tooth 5 more smoothly, and the scratch to the tooth 5 of the ratchet 2 by the vertical segment 12 is reduced.

In addition, in this embodiment, preferably, as shown in FIGS. 15 and 17, a surface 51 of each tooth 5 is obliquely extended from an inner side to an outer side of the ratchet 2 at an preset angle of inclination, and the top of each tooth 5 is located between a top end and a bottom end of an adjacent tooth 5 (as shown in FIG. 15, the top end 37 is located between the top end 18 and the bottom end 36). Wherein, when the key is pressed down, the elastic component 1 slides from the top end 18 to the bottom end 36 of a corresponding tooth 5 along the surface of this tooth, and then pushes the ratchet 2 to rotate. Thus, after the elastic component 1 touches a tooth 5 directly facing the elastic component to generate elastic deformation, the elastic component 1 can slide downward along the surface 51 of this tooth 5, and this tooth 5 is rotated along the circumferential surface of the ratchet 2 under the compression of the elastic component 1. After this tooth 5 is rotated by a certain angle until its bottom end (the bottom end 36 in FIG. 15) is exactly located below the tail end of the elastic component 1, the tail end of the elastic component 1 now exactly slides to the bottom end 36 of this tooth 5. Therefore, after the key is released and the elastic component restores to the initial position and the initial shape, the tail end of the elastic component 1 exactly faces a top end (the top end 37 in FIG. 15) of a tooth 5 adjacent to this tooth 5. Thus, after the key body 8 is pressed down again, the tail end of the elastic component 1 can slide into a socket of a tooth adjacent to this tooth 5, so it is ensured that the elastic component 1 can continuously strike different teeth 5 when the key is pressed down continuously, and the ratchet 2 is allowed to rotate continuously in a single direction.

Apparently, in this embodiment, the user may also allow the elastic component 1 to slide on the top end 18 of a corresponding tooth 5 along the surface of the tooth 5; and, when the elastic component 1 slides downward to a preset distance, without the need of reaching the bottom end, the key may be released, to allow the elastic component 1 to restore to the initial shape. When the user presses down the key again, the elastic component 1 may slide into a socket of the next tooth, and then slide along the surface of this tooth from the top end (the top end shown in FIG. 15) of this tooth. By performing this reciprocated operation, the ratchet 2 is allowed to continuously rotate in a single direction. Therefore, in this embodiment, allowing the elastic component 1 to return to the initial position after sliding from the top end to the bottom end of each tooth 5 once a user presses down the key and to slide into a socket of the next tooth, or to return to the initial position after sliding to a preset distance and then slide into the socket of the next tooth after the user presses down the key again is not specifically limited and described.

Figure 19:
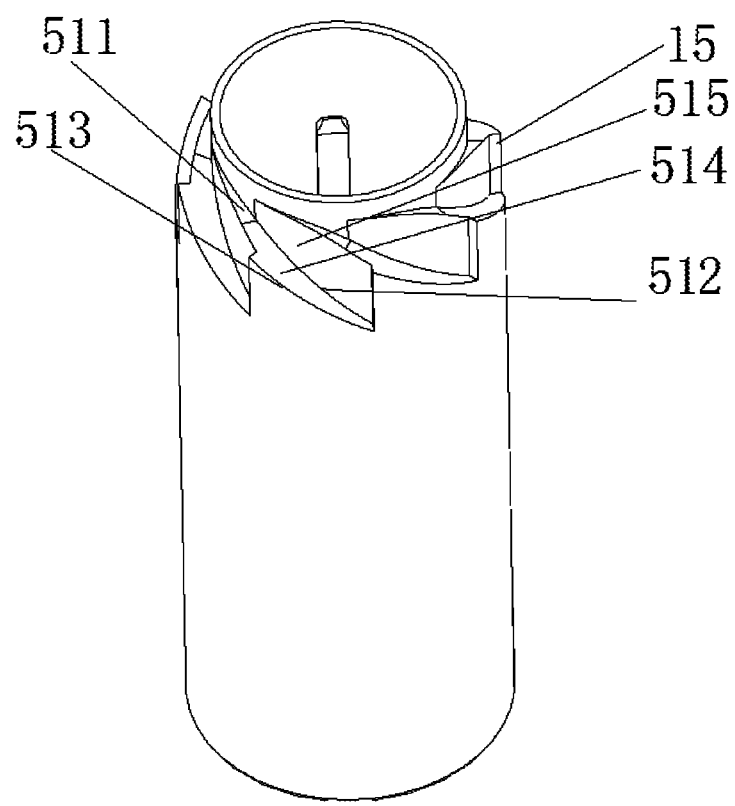
FIG. 19 is a structure diagram of a ratchet according to Embodiment 2 of the present utility model.
Figure 20:
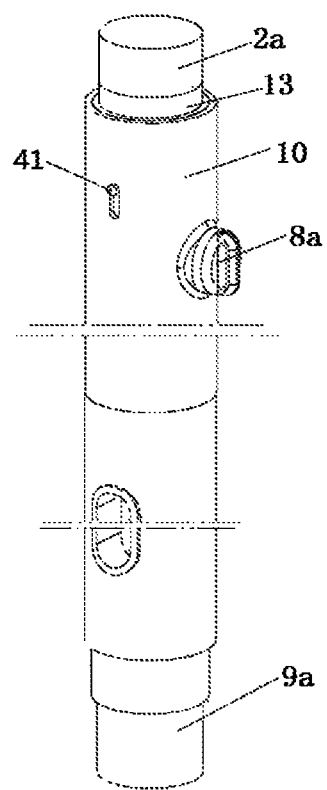
FIG. 20 is a structure diagram of a medical injection device according to Embodiment 3 of the present utility model.
Figure 21:
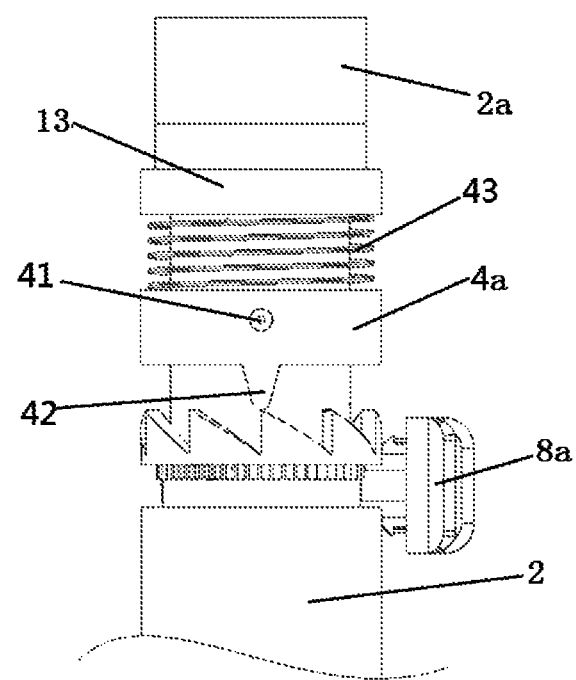
FIG. 21 is a structure diagram when a safety switch is engaged with a locking mechanism according to Embodiment 3 of the present utility model.
Figure 22:
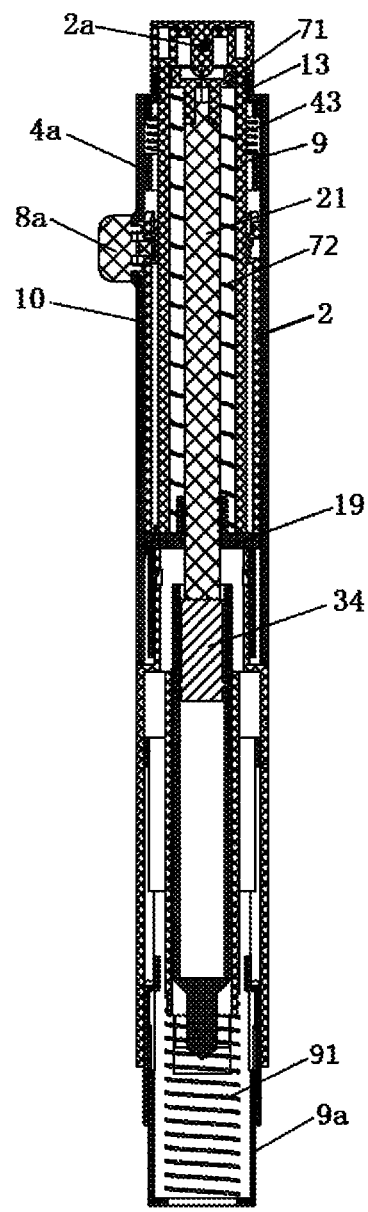
FIG. 22 is a cross-sectional view of the medical injection device according to Embodiment 3 of the present utility model.
Figure 23:
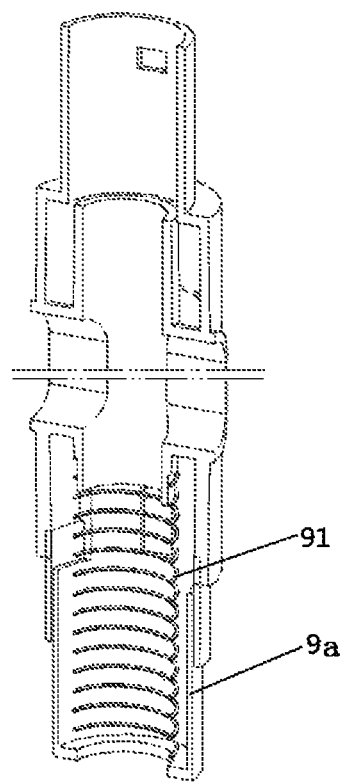
FIG. 23 is a structure diagram of a needle protection mechanism according to Embodiment 3 of the present utility model.
Figure 24:
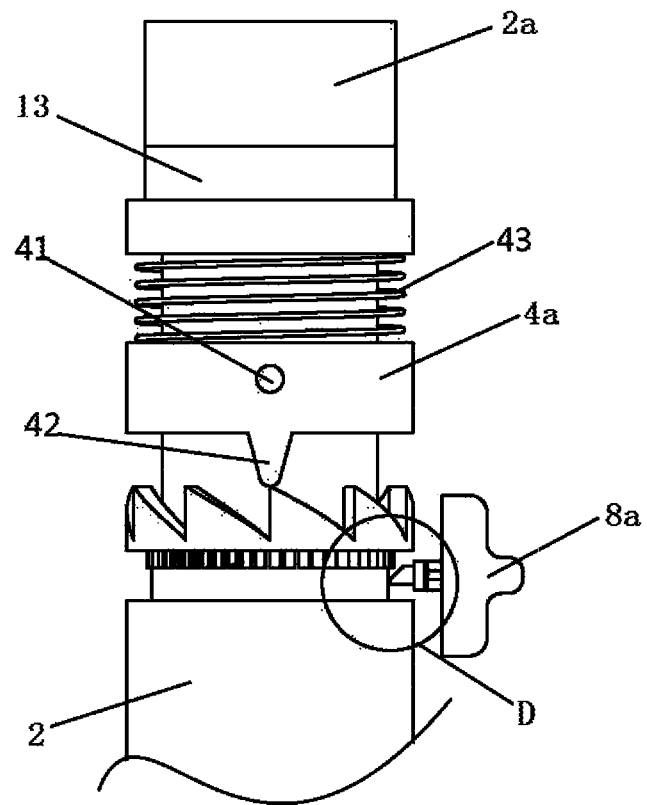
FIG. 24 is a structure diagram when the safety switch is disengaged from the locking mechanism according to Embodiment 3 of the present utility model.
Figure 25:
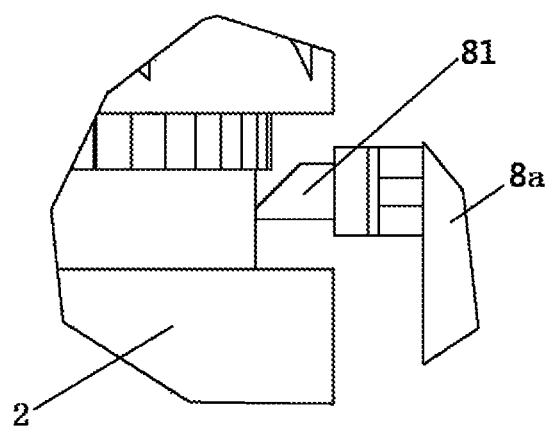
FIG. 25 is a partially enlarged view of D of FIG. 24.
Figure 26:
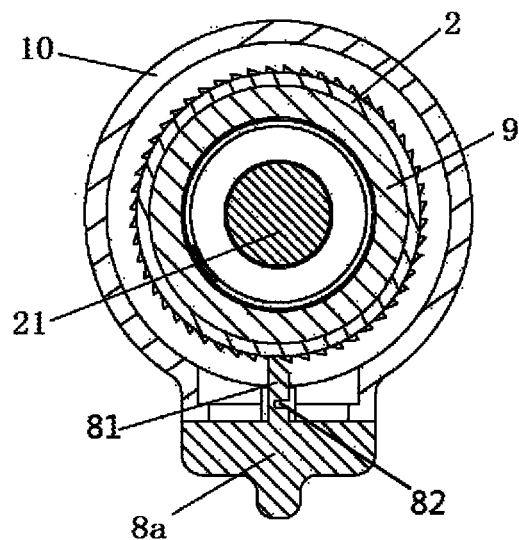
FIG. 26 is a cross-sectional view when the safety switch is engaged with the locking mechanism according to Embodiment 3 of the present utility model.

In addition, preferably, in this embodiment, as shown in FIGS. 17 and 19, the teeth of the ratchet are distributed about an axis of the ratchet 2. Furthermore, at least parts of the surfaces 51 of the teeth 5 are spiral surfaces 514, to reduce the contact area of the elastic component 1 with a surface of a corresponding tooth 5 when the elastic component 2 touches the surface of the corresponding tooth 5, and to prevent the generation of surface-to-surface contact between the elastic component and the surface of the tooth. As a result, the resistance is reduced, the elastic component 1 is stressed uniformly, and the user's feel of pressing the key is enhanced. As shown in FIG. 19, to allow the elastic component 1 to slide outward from the top end of each tooth 5 to a spiral surface 514, a cambered transition surface 511 jointed to the spiral surface 514 of each tooth 5 is further provided on the surface of each tooth 5. The surface of each tooth 5 has an outer contour line 513 and an inner contour line 512. The change in curvature of the outer contour line of each tooth 5 is identical, and the change in curvature of the inner contour line 512 of each tooth 5 is also identical. Further, parts of each outer contour line 513 and a corresponding inner contour line 512 do a spiral trajectory motion by using the center axis of the dial threaded rod 9 as a generatrix.

Further, preferably, the distance from the top end 18 to the bottom end 16 of each tooth 5 in a radial direction of the ratchet 2 is less than the maximum deformation distance of the elastic component 1, for example, the maximum offset distance of the bent segment in the radial direction of the ratchet 2 after the elastic component 1 slides from the top end 18 to the bottom end 36 of the corresponding tooth in the ratchet 2, as shown in FIG. 15. Thus, it is ensured that the elastic component 1 can smoothly slide from the top end 18 to the bottom end 36 of the corresponding tooth when the elastic component 1 touches the corresponding tooth of the ratchet 2 to generate deformation.

As shown in FIGS. 17 and 19, to prevent the elastic component 1 from sliding out from the socket of the corresponding tooth 5 of the ratchet 2 under the action of the key, a limiting groove 15 for limiting the elastic component 1 is formed on a back 515 (equivalent to a wall of the socket of each tooth) of each tooth 2 of the ratchet 2, and each limiting groove 15 is located at a position where the respective back 515 is connected to the bottom end 36 of an adjacent tooth. Meanwhile, to ensure that the elastic component 1 can smoothly slide out from the socket of the corresponding tooth 5 after the key is released, and to avoid the reverse rotation of the tooth 5, the opening direction of the limiting groove 15 is parallel to the axial direction of the ratchet 2.

As shown in FIGS. 15 and 17, to satisfy the actual design requirements, the key structure further includes a compression spring 6 which is provided within the automatic injection device and used for compressing the key. And, the compression spring 6 compresses the key toward the initial position to separate the elastic component 1 in the key from the corresponding tooth 5 of the ratchet 2 after the key is released. Wherein, the scalable length of the compression spring 6 is greater than or equal to a distance from the top end to the bottom end of the corresponding tooth in the axial direction of the ratchet 2.

As described above, after the key is released, through the resilience performance of the compression spring 6, the elastic component 1 can slide from the top end 18 to the bottom end 36 of the corresponding tooth 5 of the ratchet 2 under the elastic action of the compression spring 6 without any manual operation, and can be automatically restored to the initial position after separating from the corresponding tooth 5 so that the elastic component 1 restores to the initial shape. Moreover, after a key body 8 is pressed down again, the elastic component 1 can be pressed toward a next tooth in the compression direction of the compression spring 6 according to the set trajectory.

Figure 18:
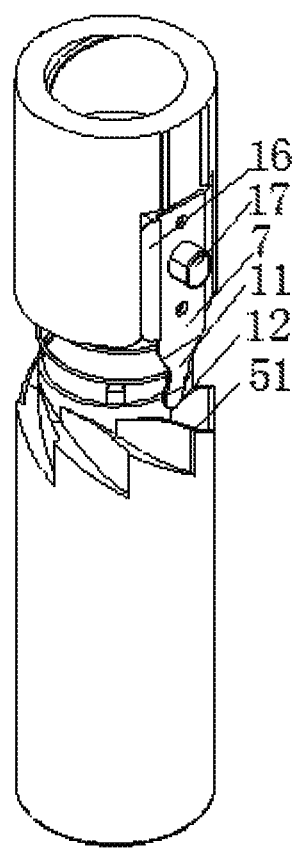
FIG. 18 is a structure diagram of an elastic component according to Embodiment 2 of the present utility model.

Furthermore, in this embodiment, as a preferred implementation, as shown in FIGS. 17 and 18, the key mainly consists of a connector 7 connected to the elastic component 1, and a key body 8 in snap-in connection to the connector 7. Wherein, the compression spring 6 is sheathed on the dial threaded rod 9 and resisted against one end of the connector 7. Apparently, in this embodiment, the compression spring 6 may also be directly resisted against the connector 7, and this will not be specifically limited and described in this embodiment.

Furthermore, as shown in FIGS. 15 and 17, a groove 14 for accommodating the key body 8 is formed on the first end cover 13, and the length of the groove 14 is greater than that of the key body 8. To be convenient for a user to press the key body 8, the key body 8 can stably do a reciprocating motion within the groove 14.

Furthermore, as shown in FIG. 18, to be convenient for assembly in practical applications, preferably, a slider 16 in fitted connection to the connector 7 is further provided within the groove 14, and the slider 16 is slidingly provided within the groove 14. Meanwhile, threaded holes (not shown) for allowing fasteners to be inserted therein are formed on the connector 17 and the slider 16. Furthermore, a portion of the connector 7 is hollowed out and used for passing a connection portion 17 therethrough, so that the connector is in snap-in connection to the key body 8 through the connection portion 17.

In addition, in this embodiment, as shown in FIG. 8, at least one portion of the key body 8 is exposed from the housing 10 when the first end cover 13 is covered by the housing 10 of the automatic injection device, and the exposed portion of the key body 8 has a recessed portion for coordinating with the pressing by a thumb.

Thus, it is not difficult to find that, by coordinating with the pressing by a thumb by using the recessed portion of the key body 8, it is convenient for a user's operation, and the user experience may be improved, so that the experience of using the automatic injection device with the key is improved.

Figure 2:
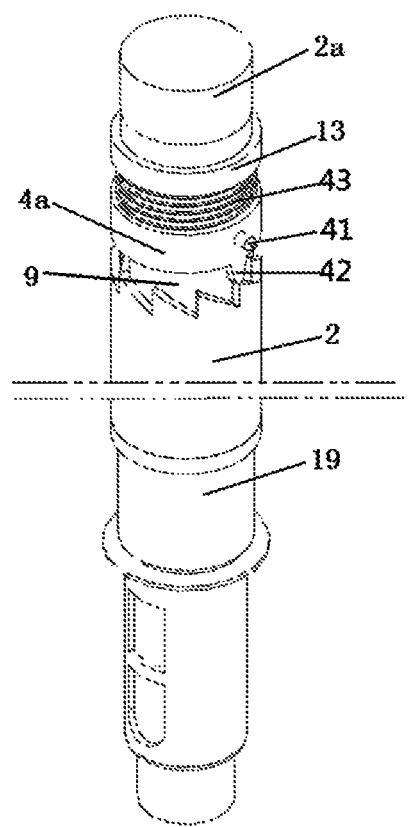
FIG. 2 is a schematic structure diagram of FIG. 1, with a housing omitted.
Figure 3:
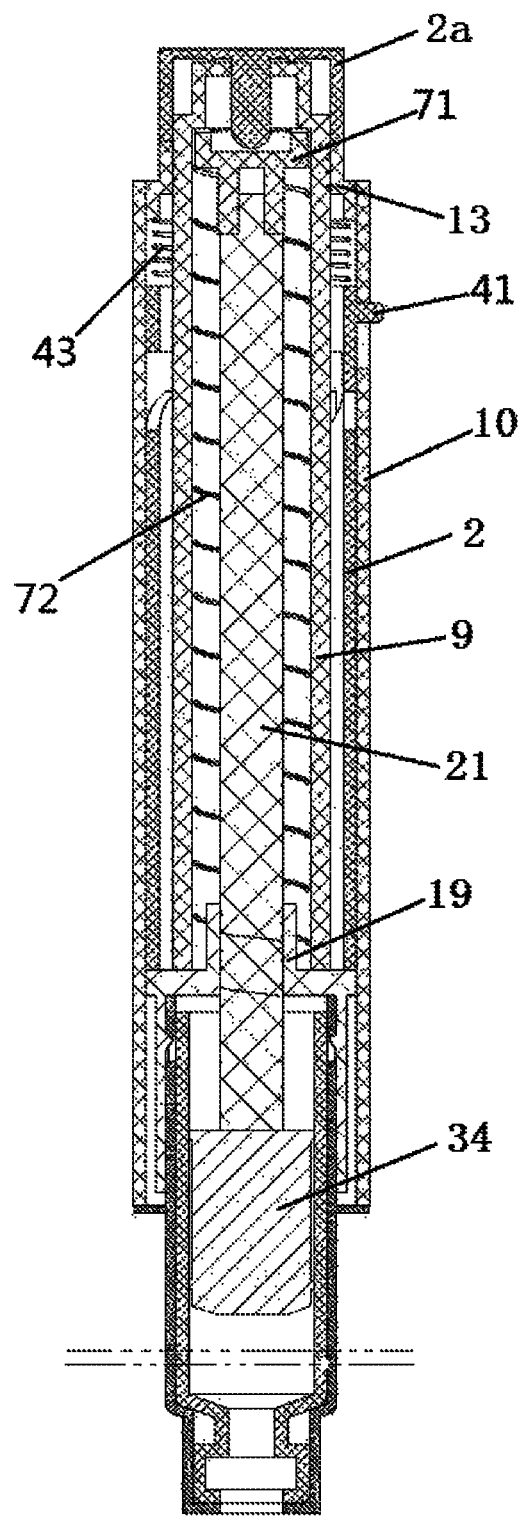
FIG. 3 is a cross-sectional view of the medical injection device according to Embodiment 1 of the present utility model.
Figure 4:
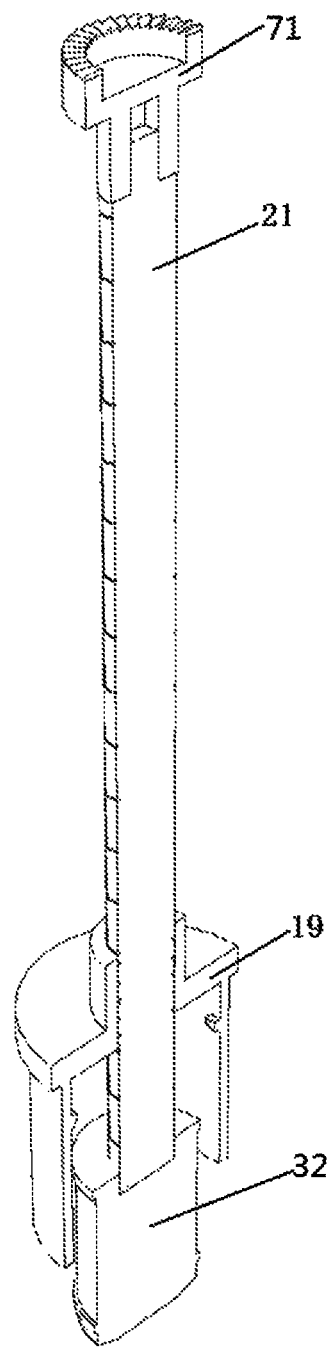
FIG. 4 is a cross-sectional structure diagram of the connection of a piston rod to a driving member and to a second end cover according to Embodiment 1 of the present utility model.
Figure 5:
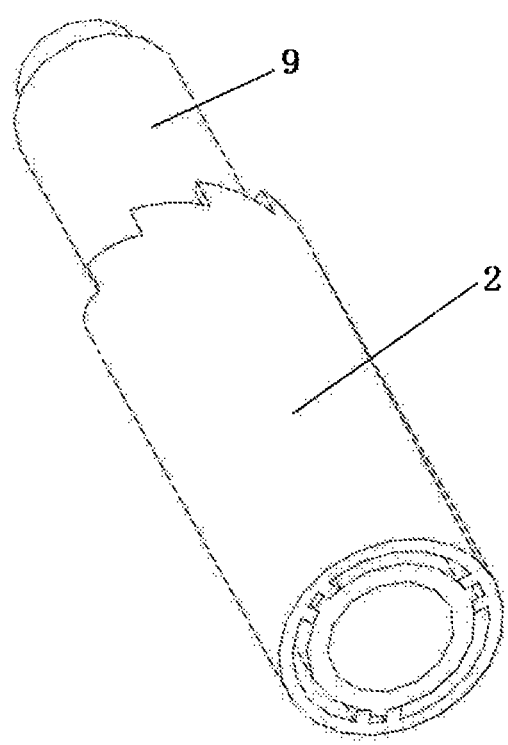
FIG. 5 is a structure diagram of the connection of a ratchet to a dial threaded rod according to Embodiment 1 of the present utility model.
Figure 6:
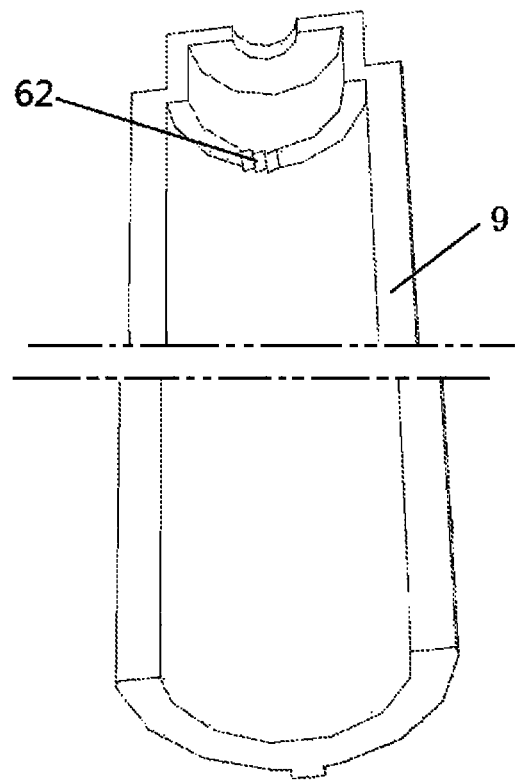
FIG. 6 is a structure diagram of the dial threaded rod according to Embodiment 1 of the present utility model.

Meanwhile, it is to be noted that, the working principle of this embodiment is roughly as follows: when the automatic injection device leaves the factory, the piston rod 21 is located at an initial position, i.e., the highest portion in the first sleeve 20, and the cap 30 is fitted with the first end cover 13 in this case; therefore, when a user operates the automatic injection device, as shown in FIG. 2, according to the dosage per injection, the ratchet 2 is allowed to rotate in a single direction through the elastic component 1 of the key, so that the dial threaded rod 9 realizes synchronous rotation with the ratchet 2 under the action of the guide grooves and the bulges of the ratchet 2 (through the mutual fitting of a plurality of guide grooves and the corresponding bulges) and in virtue of the fitted connection of the external threads provided on the outer wall of the dial threaded rod and the internal threads on the through hole of the first end cover 13. After the ratchet 2 is rotated by a certain angle, the dial threaded rod 9 is extended outward a certain displacement relative to the first end cover 13. This displacement is embodied by the scale on the surface of the dial threaded rod 9. When the user has adjusted the scale and then pressed down the gland 31, the dial threaded rod 9 may be driven to rotate in an opposite direction under the action of the gland 31 and the cap 30 until the cap 30 is fitted to the first end cover 13 again. In this way, the injection of the adjusted dosage is completed, and the dose is prevented from being expelled in an excessive amount. In this case, the dial threaded rod 9 is retracted into the first end cover 13.

However, when the dial threaded rod is rotated in an opposite direction, the teeth 25 of the dial threaded rod 9 are engaged with the teeth 26 on the second sleeve 22, so that the second sleeve 22 and the first sleeve 20 in sliding connection to the second sleeve 22 are driven to rotate. During the rotation of the first sleeve 20, due to the torque between the inner wall of the cavity of the first sleeve 20 and the driving portion 211 of the piston rod 21, the piston rod 21 is directly driven to rotate synchronously. Moreover, during the rotation of the piston rod 21, through the fitted connection of the external threads provided on the outer wall of the piston rod 21 and the internal threads provided on the through hole of the second end cover 19, the piston rod 21 drives the piston 34 to move down relative to the vial, so that the medicine liquid at the designed dosage is expelled. Since the dosage expelled every time is the same as the adjusted dosage, the fineness of the expelled dosage is improved.

The present utility model further provides a second embodiment. The second embodiment is basically the same as Embodiment 1, expect for the following difference: at least parts of the surfaces 51 of the teeth 5 of the ratchet 2 are spiral surfaces 514 in Embodiment 1, while the surfaces of the teeth 5 of the ratchet 2 are oblique planes.

Thus, in this embodiment, since the surfaces of the teeth of the ratchet 2 are oblique planes, the guidance of the elastic component 1 can also be realized, and the ratchet 2 can be pushed to rotate when touched by the elastic component 1; and, after the key is released and the elastic component 1 restores to the initial shape, the elastic component slides into a socket of an adjacent tooth when the key is pressed down again, so that the rotation of the ratchet 2 in a single direction is realized. Accordingly, the effects achieved by the surfaces 51 of the teeth in Embodiment 1 can also be realized.

Embodiment 3

As shown in FIGS. 20 to 27, Embodiment 3 of the present utility model further provides a medical injection device. The medical injection device in this embodiment is a further improvement based on Embodiment 1 or Embodiment 2, and has the following differences from Embodiment 1 and Embodiment 2: in this embodiment, a protection mechanism for limiting the rotation of the ratchet 2 is provided on the housing 10; the protection mechanism includes a safety switch 8a and a locking mechanism, wherein the locking mechanism is locking teeth arranged on a circumferential surface of the ratchet 2; wherein the safety switch 8a is rotatably arranged within a mounting hole on a side wall of the housing 10, so that a latch 81 of the safety switch 8a is engaged with or disengaged from the locking teeth after the safety switch 8a is rotated. In practical productions and applications, the safety switch 8a is snapped to the mounting hole on the side wall of the housing 10 through a hasp.

Specifically, the guide grooves are arranged on the circumferential surface of the ratchet 2 in such a way that the guide grooves are extended along the circumference of the ratchet 2, and the latch 81 of the safety switch 8a is extended to a tooth surface of a guide groove. When the safety switch 8a is rotated, the latch 81 is engaged with or disengaged from the guide groove.

Figure 27:
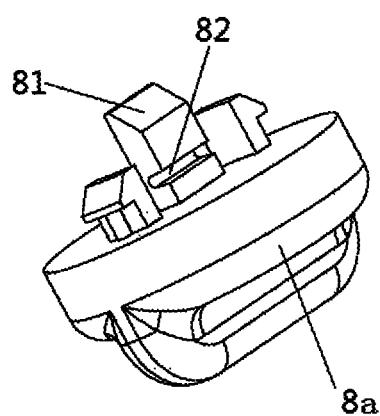
FIG. 27 is a structure diagram of the safety switch according to Embodiment 3 of the present utility model.

To prevent the inverse rotation of the ratchet 2 during the dosage adjustment, the latch 81 is of a pawl structure with unidirectional elastic deformation. Specifically, for example, the latch 81 is in shape of a stopper. As shown in FIG. 27, when the latch 81 is engaged with the teeth of the locking ratchet, a check groove 82 is formed on a side of the latch 81 in a transverse direction of the latch 81.

The medical injection device in this embodiment is similar to the structure of Embodiment 1 and Embodiment 2. In this embodiment, the inventive points of this embodiment will be described based on the structure of Embodiment 1. The medical injection device in this embodiment mainly includes a housing 10, a vial which is arranged at one end of a cavity of a through hole of the housing 10 and has a piston 34, and a trigger switch button 2a. A first end cover 13 is provided at an upper end of the housing 10, while a second end cover 19 is provided a lower end thereof. The second end cover 12 is snapped at a lower end of a cavity of a through hole of the housing 10. Through holes are formed in both the middle of the first end cover 13 and the middle of the second end cover 19. The vial is fixed at a lower end of the housing 10 through a vial sleeve, and an upper end of the vial sleeve is snapped into the second end cover 19. A dose dosage adjustment mechanism includes an adjustment key 4a and a ratchet 2. The ratchet 2 is embedded into the cavities of the through holes of the housing 10. The ratchet 2 is sheathed on the dial threaded rod 9 and is in torque connection to the dial threaded rod 9, so that the both can slide relative to each other in the axial direction. In this embodiment, guide grooves are provided on an inner side wall of the ratchet 2 in the axial direction, and bulges in sliding connection to the guide grooves are provided an outer wall of the dial threaded rod 9. By fitting the guide grooves with the bulges, torque transmission is formed between the dial threaded rod 9 and the ratchet 2, and the bugles slide within the guide grooves when the ratchet 2 and the dial threaded rod 9 are rotated. To realize uniform stress and smooth adjustment, there are three guide grooves uniformly distributed on a circumferential surface of the ratchet 2. A tooth surface of the ratchet 2 is connected to the adjustment key 4a, and the ratchet 2 is driven to rotate in a single direction by driving the adjustment key 4a. External threads are provided on the outer wall of the dial threaded rod 9. The external threads are in fitted connection to internal threads on the through hole in the middle of the first end cover 13. An upper end of the dial threaded rod 9 is connected to the trigger switch button 2a, while a lower end thereof is connected to a driving member 71. A lower end of the driving member 71 is connected to the piston rod 21 in a torque transmission manner. Specifically, the driving member 71 is sheathed on a square rod at the upper end of the piston rod 21 to transfer torque. External threads are provided on an outer wall of the piston rod 21, and the external threads are in fitted connection to internal threads in the through hole in the middle of the second end cover 19.

Wherein, a circle of first ratchets having upward tooth surfaces are formed on an upper end face of the driving member 71 along the circumference of the driving member 71, and pawls 62 matched with the first ratchets are provided on the dial threaded rod 9. In this embodiment, the dial threaded rod 9 is sheathed on the piston rod 21; upper ends of both the driving member 21 and the piston rod 21 are located within a cavity of the dial threaded rod 9; the pawls 62 are provided on a top wall of the cavity of the dial threaded rod 9; and, a compression spring 72 used for allowing the first ratchets at the upper end of the driving member 71 and the pawls 62 on the top wall of the cavity of the dial threaded rod 9 to be always engaged with each other is provided between the lower end of the driving member 71 and the second end cover 19. When the trigger switch button 2a is pressed down to drive the dial threaded rod 9 to descend spirally after the dosage is adjusted, due to the engagement of the first ratchets with the pawls 62, the piston rod 21 will simultaneously rotate, so that the adjusted dosage is ensured to be the same as the amount of the expelled and injected dose.

As a preferred implementation of the present utility model, the teeth of the ratchet 2 are arranged on an upper end face of the ratchet 2 in such a way that the teeth are extended in a circumferential direction of the ratchet 2, wherein the direction of inclination of tooth surfaces of the ratchet 2 is the same as that of tooth surfaces of the first ratchets.

The adjustment key 4a is sheathed on the dial threaded rod 9. A protrusion 42 is formed at a lower end of the adjustment key 4a, and a tip portion of the protrusion 42 may be fitted onto a tooth surface of the ratchet 2 in the presence of an external force. A strip-shaped through hole arranged in the axial direction of the housing 10 is formed on a side wall of the housing 10. A bump 4141 extending through the strip-shaped through hole is formed on a side wall of the adjustment key 4a. The bump 41 is extended to an outer side of the housing 10. The bump 41 is convenient for a finger of a user to apply an external force to the bump, so as to drive the adjustment key 4a to move in the axial direction of the housing 10 as a whole. Of course, other structures convenient for driving the adjustment key 4a to move may also be used to replace the bump 41. For the convenience of operation, a tension spring 43 is provided between the upper end of the adjustment key 4a and the first end cover 13. When the adjustment key 4a is moved to the lowest position of the strip-shaped through hole and after the external force is released, under the action of the tension spring 43, the adjustment key 4a may automatically restore to the highest point of the strip-shaped through hole to get ready for the next adjustment.

Specifically, the guide grooves are arranged on the circumferential surface of the ratchet 2 in such a way that the guide grooves are extended along the circumference of the ratchet 2; a safety switch 8a is snapped in a mounting hole on a side wall of the housing 10 through a hasp; a latch 81 of the safety switch 8a is extended to a tooth surface of a guide groove; and, when the safety switch 8a is rotated, the latch 81 is engaged with or disengaged from the guide groove.

To prevent the inverse rotation of the ratchet 2 during the dosage adjustment, the latch 81 is of a pawl structure with unidirectional elastic deformation. Specifically, for example, the latch 81 is in shape of a stopper. As shown in FIG. 27, when the latch 81 is engaged with the teeth of the locking ratchet, a check groove 82 is formed on the latch 81 in a transverse direction of the latch 81.

In this embodiment, preferably, the medical injection device further includes a needle shield 9a and a shield resetting member 91; the needle shield 9a can slide relative to a wall of an inner cavity of the vial sleeve and is embedded at a lower end of the inner cavity of the vial sleeve; and the shield resetting member 91 is arranged between the needle shield 9a and the wall of the inner cavity of the vial sleeve, and used for extruding the needle shield 9a into the vial sleeve in the presence of an external force and urging the needle shield 9a to extend out from the vial sleeve after the external force is released, wherein the shield resetting member 91 is a spring having one end connected to the inner wall of the vial sleeve and the other end connected to the needle shield 9a.

The working principle of this embodiment is as follows.

During the adjustment of the dosage, the adjustment key 4a is driven to move down, and the protrusion 42 of the adjustment key 4a is resisted against a tooth surface at the upper end of the ratchet 2 to drive the ratchet 2 to rotate in a single direction. The dial threaded rod 9 synchronously rotates with the ratchet 2 under the action of the bulges and the guide grooves. The external threads arranged on the outer wall of the dial threaded rod 9 are in fitted connection to the internal threads arranged on the through hole of the first end cover 13. After the ratchet 2 is rotated by a certain angle, the dial threaded rod 9 is extended outward a certain displacement relative to the first end cover 13. This displacement is embodied by the scale on the surface of the dial threaded rod 9. After the dosage is adjusted, the safety switch 8a is rotated to engage the latch 81 with the guide grooves, so as to limit the inverse rotation of the ratchet 2 and the dial threaded rod 9.

During the injection, the safety switch 8a is rotated to disengage the latch 81 from the guide grooves, and the trigger switch button 2a is pressed down. The trigger switch button 2a drives the dial threaded rod 9 to rotate in an opposite direction to retract into the first end cover 13. The pawls 62 of the dial threaded rod 9 are engaged with the first ratchets on the upper end face of the driving member 71, so that the piston rod 21 is driven to rotate synchronously. Since the external threads arranged on the outer wall of the piston rod 21 are in fitted connection to the internal threads arranged on the through hole of the second end cover 19, the piston rod 21 drives the piston 34 to move down relative to the vial, so that the medicine liquid at the desired dosage is expelled.

It should be understood that, the nouns of locality are defined according to the daily operation habits of an operator and a user and the accompanying drawings of the specification, and the presence of the nouns of locality shall not influence the protection scope of the present utility model.

Although the present utility model has been described above in detail with reference to the accompanying drawings and embodiments, a person of ordinary skill in the art may make various variations to the present utility model according to the forgoing description. Therefore, some details in the embodiments shall not constitute any limitations to the present utility model, and the protection scope of the present utility model shall be subject to the scope defined by the appended claims.

What is claimed is:

1. A medical injection device, comprising:
    a housing having a first end cover and a second end cover provided at two ends thereof, respectively;
    a dial threaded rod, which is in threaded connection to the first end cover; and
    a piston rod, which is used for expelling a dose, an upper end of the piston rod being connected to the dial threaded rod through a driving mechanism while a lower end thereof being in threaded connection to the second end cover;
    characterized in that the medical injection device further comprises a dosage adjustment mechanism which is arranged between the dial threaded rod and the housing and used for driving the dial threaded rod to move in an axial direction of the housing; and
    when the dial threaded rod ascends spirally, the driving mechanism at least partially ascends straightly along with the dial threaded rod; and, when the dial threaded rod descends spirally, the driving mechanism at least partially does a spiral descending motion along with the dial threaded rod, and drives the piston rod to synchronously do a spiral descending motion.

2. The medical injection device according to claim 1, characterized in that the dosage adjustment mechanism comprises an adjustment key and a ratchet; the adjustment key is slidingly arranged on the housing and used for driving the ratchet to rotate; and, the ratchet is sheathed on the dial threaded rod and used for driving the dial threaded rod to rotate.

3. The medical injection device according to claim 2, characterized in that the ratchet is in torque connection to the dial threaded rod;

wherein the adjustment key is sheathed on the dial threaded rod; a protrusion at a lower end of the adjustment key is fitted onto teeth of the ratchet in the presence of an external force; a strip-shaped through hole arranged in the axial direction of the housing is formed on a side wall of the housing; and a bump extending through the strip-shaped through hole is formed on a side wall of the adjustment key; and when pressed down, the adjustment key is coordinated with the teeth of the ratchet to drive the ratchet to rotate in a single direction, and the dial threaded rod synchronously rotates under the action of the ratchet.

4. The medical injection device according to claim 2, characterized in that a tension spring for resetting the adjustment key is provided between the upper end of the adjustment key and the first end cover.

5. The medical injection device according to claim 1, characterized in that the driving mechanism comprises:
a driving member, which is in torque connection to the piston rod; and
an elastic pressing member, which is resisted against a lower end of the driving member and used for maintaining the engagement of the dial threaded rod with the driving member through a ratchet mechanism; and
when the dial threaded rod ascends spirally, the driving member ascends straightly along with the dial threaded rod under the action of the elastic pressing member, and slides relative to the piston rod; and, when the dial threaded rod descends spirally, the dial threaded rod drives the driving member to rotate through the engagement by the ratchet mechanism, and the piston rod does a spiral descending motion along with the rotation of the driving member.

6. The medical injection device according to claim 5, characterized in that the teeth of the ratchet are arranged on a circumferential surface of the ratchet in such a way that the teeth are extended in a circumferential direction of the ratchet; and
the ratchet mechanism comprises: teeth arranged on a circumferential surface of the driving member and pawls arranged on an inner wall of the dial threaded rod, the pawls being matched and engaged with the teeth, the direction of inclination of tooth surfaces of the teeth of the ratchet being opposite to that of tooth surfaces of the teeth of the driving member.

7. The medical injection device according to claim 5, characterized in that the teeth of the ratchet are arranged on an upper end face of the ratchet in such a way that the teeth are extended in a circumferential direction of the ratchet; and
the ratchet mechanism comprises: teeth arranged on an upper end face of the driving member and pawls arranged on the dial threaded rod, the pawls being matched and engaged with the teeth, the direction of inclination of tooth surfaces of the teeth of the ratchet being the same as that of tooth surfaces of the teeth of the driving member.

8. The medical injection device according to claim 1, characterized in that the medical injection device further comprises a vial and a trigger switch button; the vial is arranged at the lower end of the housing, and a piston connected to the piston rod is provided inside the vial; and, the trigger switch button is connected to the upper end of the dial threaded rod.

9. The automatic injection device with an adjustable dosage according to claim 8, characterized in that the vial is fixed at the lower end of the housing through a vial sleeve; a lower end of the vial sleeve is snapped into the second end cover; and, the second end cover is snapped at the lower end of a cavity of the through hole of the housing.

10. The automatic injection device with an adjustable dosage according to claim 1, characterized in that a plurality of guide grooves are provided on an inner side wall of the ratchet in an axial direction of the ratchet; the guide grooves are uniformly distributed on a circumferential surface of the ratchet; and, bulges in sliding connection to the guide grooves are formed on an outer wall of the dial threaded rod.

11. The medical injection device according to claim 1, characterized in that the driving mechanism comprises a first sleeve and a driving member;
the first sleeve is sheathed on the piston rod and used for driving the piston rod to rotate;
the driving member is arranged within a cavity of the dial threaded rod and resisted against an elastic pressing member arranged above the second end cover, the driving member is used for driving the first sleeve to rotate, and the dial threaded rod and the driving member are engaged with each other through a ratchet mechanism under the pressing of the elastic pressing member;
when the dial threaded rod ascends spirally, the driving member ascends straightly under the action of the elastic pressing member; and
when the dial threaded rod descends spirally, the driving member drives the first sleeve to rotate through the engagement by the ratchet mechanism, and the piston rod does a spiral descending motion along with the rotation of the first sleeve;
wherein a second sleeve is in sliding connection to an upper end of the first sleeve, and the second sleeve slides in an axial direction of the dial threaded rod when the dial threaded rod ascends spirally.

12. The medical injection device according to claim 11, characterized in that a boss is provided at an upper end of the second sleeve;
a neck matched with the boss is provided at an upper end of the first sleeve;
wherein, when the dial threaded rod ascends spirally, the boss slides upward within the neck; and, when the dial threaded rod descends spirally, the boss slides downward within the neck and drives the second sleeve to rotate.

13. The medical injection device according to claim 12, characterized in that the maximum displacement of a relative slip generated between the boss and the neck is less than or equal to the length of external threads on the dial threaded rod.

14. The medical injection device according to claim 12, characterized in that the piston rod comprises: a driving portion arranged within a cavity of the first sleeve, and a threaded segment connected to the driving portion;
wherein the section of the driving portion is matched in shape and size with the section of the cavity of the first sleeve; and the driving portion synchronously rotates when the first sleeve rotates, and is fitted with threads of the second end cover through the threaded segment.

15. The medical injection device according to claim 11, characterized in that the ratchet mechanism comprises: first teeth provided on the top of the cavity of the dial threaded rod, and second teeth provided on the top of the second sleeve and fitted with the first teeth;
wherein both the first teeth and the second teeth are distributed circumferentially.

16. The medical injection device according to claim 11, characterized in that a first resisting portion and a second resisting portion used for resisting against the elastic pressing member are provided at the lower end of the first sleeve and the lower end of the second sleeve, respectively;
wherein the elastic pressing member is arranged between the first resisting portion and the second resisting portion, and the first resisting portion and the second resisting portion are always resisted against the elastic pressing member.

17. The medical injection device according to claim 10, further comprising: a cap which is arranged within a through hole of the first end cover and buckled with the upper end of the dial threaded rod, and a gland arranged on the cap;
wherein a fixed shaft is provided in a center of the gland, and the fixed shaft is inserted into the cavity of the dial threaded rod through a hollow portion of the cap.

18. The medical injection device according to claim 17, characterized in that a convex ring used for contacting and pressing the cap is provided on the top of an inner surface of the gland.

19. The medical injection device according to claim 11, characterized in that the second end cover and the housing are formed integrally, and an end face of the second end cover is resisted against the bottom of the first sleeve.

20. The medical injection device according to claim 1, characterized in that the dosage adjustment mechanism comprises: a ratchet for driving the dial threaded rod to rotate, and a key which is slidingly provided on the first end cover and used for driving the ratchet to rotate; and
at least part of the key is an elastic component used for being inserted into a socket of a tooth of the ratchet;
wherein the teeth of the ratchet are distributed about an axis of the ratchet; and
after the key is pressed down, the elastic component touches the teeth to generate elastic deformation, slides into the socket of the tooth, and pushes the ratchet to rotate; and, the elastic component can be restored to an initial shape after the key is released, and can slide into a socket of a tooth adjacent to the tooth to push the ratchet to rotate in a single direction after the key is pressed down again.

21. The medical injection device according to claim 20, characterized in that a surface of each tooth is obliquely extended from an inner side to an outer side of the ratchet, and the top of each tooth is located between a top end and a bottom end of an adjacent tooth;
wherein, when the key is pressed down, the elastic component slides from the top end to the bottom end of a corresponding tooth along the surface of this tooth, and then pushes the ratchet to rotate.

22. The medical injection device according to claim 21, characterized in that at least parts of the surfaces of the teeth of the ratchet are spiral surfaces, or the surfaces of the teeth of the ratchet are oblique planes.

23. The medical injection device according to claim 20, characterized in that a limiting groove for limiting the elastic component is formed on a back of each tooth, and each limiting groove is located at a position where the respective tooth back is connected to the bottom end of an adjacent tooth.

24. The medical injection device according to claim 20, characterized in that the medical injection device further comprises a compression spring which is provided within the housing and used for compressing the key; and the compression spring compresses the key toward an initial position to separate from the corresponding tooth after the key is released;
wherein the scalable length of the pressing spring is greater than or equal to a distance from the top end to the bottom end of the corresponding tooth in an axial direction of the ratchet.

25. The medical injection device according to claim 20, characterized in that the elastic component comprises a bent segment and a vertical segment connected to the bent segment, and the vertical segment is parallel to the axial direction of the ratchet.

26. The medical injection device according to claim 25, characterized in that a portion of the vertical segment facing the ratchet is a curved surface, and the width of the vertical segment gradually decreases from one end thereof connected to the bent segment to its bottom end.

27. The medical injection device according to claim 20, characterized in that the key comprises: a connector connected to the elastic component, and a key body in snap-in connection to the connector, with the connector being resisted against the compression spring.

28. The medical injection device according to claim 27, characterized in that the key structure further comprises an end cover; a groove for accommodating the connector is formed on the end cover; and the length of the groove is greater than that of the connector.

29. The medical injection device according to claim 1, characterized in that the medical injection device further comprises a protection mechanism for limiting the rotation of the ratchet, the protection mechanism comprises a safety switch and a locking mechanism, and the locking mechanism is locking teeth arranged on a circumferential surface of the ratchet; and
the safety switch is rotatably arranged within a mounting hole on a side wall of the housing, so that a latch of the safety switch is engaged with or disengaged from the locking teeth after the safety switch is rotated.

30. The medical injection device according to claim 29, characterized in that the safety switch is snapped in the mounting hole on the side wall of the housing through a hasp.

31. The medical injection device according to claim 8, further comprising a needle shield and a shield resetting member;
the vial is fixed at the lower end of the housing through a vial sleeve;
an upper end of the vial sleeve is snapped in the second end cover, and the needle shield can slide relative to a wall of an inner cavity of the vial sleeve and is embedded at an lower end of the inner cavity of the vial sleeve; and
the shield resetting member is arranged between the needle shield and the wall of the inner cavity of the vial sleeve, and used for extruding the needle shield into the vial sleeve in the presence of an external force and urging the needle shield to extend out from the vial sleeve after the external force is released.

32. The medical injection device according to claim 31, characterized in that the second end cover is snapped at the lower end of the cavity of the through hole of the housing.

33. The medical injection device according to claim 32, characterized in that the dosage adjustment mechanism comprises: a ratchet for driving the dial threaded rod to rotate, and a key which is slidingly provided on the first end cover and used for driving the ratchet to rotate; and at least part of the key is an elastic component used for being inserted into a socket of a tooth of the ratchet;

wherein the teeth of the ratchet are distributed about an axis of the ratchet; and after the key is pressed down, the elastic component touches the teeth to generate elastic deformation, slides into the socket of the tooth, and pushes the ratchet to rotate; and, the elastic component can be restored to an initial shape after the key is released, and can slide into a socket of a tooth adjacent to the tooth to push the ratchet to rotate in a single direction after the key is pressed down again.

34. The medical injection device according to claim 33, characterized in that a surface of each tooth is obliquely extended from an inner side to an outer side of the ratchet, and the top of each tooth is located between a top end and a bottom end of an adjacent tooth;

wherein, when the key is pressed down, the elastic component slides from the top end to the bottom end of a corresponding tooth along the surface of this tooth, and then pushes the ratchet to rotate.

35. The medical injection device according to claim 34, characterized in that at least parts of the surfaces of the teeth of the ratchet are spiral surfaces, or the surfaces of the teeth of the ratchet are oblique planes.

36. The medical injection device according to claim 33, characterized in that a limiting groove for limiting the elastic component is formed on a back of each tooth, and each limiting groove is located at a position where the respective tooth back is connected to the bottom end of an adjacent tooth.

37. The medical injection device according to claim 33, characterized in that the medical injection device further comprises a compression spring which is provided within the housing and used for compressing the key; and the compression spring compresses the key toward an initial position to separate from the corresponding tooth after the key is released;

wherein the scalable length of the pressing spring is greater than or equal to a distance from the top end to the bottom end of the corresponding tooth in an axial direction of the ratchet.

38. The medical injection device according to claim 33, characterized in that the elastic component comprises a bent segment and a vertical segment connected to the bent segment, and the vertical segment is parallel to the axial direction of the ratchet.

39. The medical injection device according to claim 38, characterized in that a portion of the vertical segment facing the ratchet is a curved surface, and the width of the vertical segment gradually decreases from one end thereof connected to the bent segment to its bottom end.

40. The medical injection device according to claim 33, characterized in that the key comprises: a connector connected to the elastic component, and a key body in snap-in connection to the connector, with the connector being resisted against the compression spring.

41. The medical injection device according to claim 40, characterized in that the key structure further comprises an end cover; a groove for accommodating the connector is formed on the end cover; and the length of the groove is greater than that of the connector.

\* \* \* \* \*